(12) United States Patent
Vaz et al.

(10) Patent No.: US 11,452,490 B2
(45) Date of Patent: Sep. 27, 2022

(54) METHODS AND SYSTEMS FOR AN ADAPTIVE PERFUSION SCAN

(71) Applicant: GE Precision Healthcare LLC, Milwaukee, WI (US)

(72) Inventors: Michael Sarju Vaz, Milwaukee, WI (US); Bradley J. Gabrielse, Brookfield, WI (US); Ryan C. Forbes, Hartland, WI (US); John Fusco, Waukesha, WI (US); David Joseph Pitterle, Waukesha, WI (US); John Howard Londt, Oconomowoc, WI (US); Xiaoqing Guo, Brookfield, WI (US)

(73) Assignee: GE Precision Healthcare LLC, Milwaukee, WI (US)

( * ) Notice: Subject to any disclaimer, the term of this patent is extended or adjusted under 35 U.S.C. 154(b) by 391 days.

(21) Appl. No.: 16/698,291

(22) Filed: Nov. 27, 2019

(65) Prior Publication Data
US 2021/0153830 A1 May 27, 2021

(51) Int. Cl.
*G06K 9/00* (2022.01)
*A61B 6/00* (2006.01)
(Continued)

(52) U.S. Cl.
CPC ............. *A61B 6/481* (2013.01); *A61B 6/469* (2013.01); *A61B 6/484* (2013.01); *A61B 6/488* (2013.01);
(Continued)

(58) Field of Classification Search
USPC ................ 382/100, 103, 106, 128–134, 156, 382/172–173, 219, 254, 274, 276,
(Continued)

(56) References Cited

U.S. PATENT DOCUMENTS 5,400,378 A * 3/1995 Toth ................... A61B 6/488
378/118
6,023,494 A 2/2000 Senzig et al.
(Continued)

FOREIGN PATENT DOCUMENTS

CN 101277648 A 10/2008

OTHER PUBLICATIONS

"The ONE Guides—4D Neurological Imaging," Cannon Medical Systems USA Website, Available Online at https://us.medical.canon/download/aq-one-club-guide-4d-neuro-imaging, Available Online at Early as Jan. 2010, 16 pages.
(Continued)

*Primary Examiner* — Seyed H Azarian
(74) *Attorney, Agent, or Firm* — McCoy Russell LLP

(57) ABSTRACT

Methods and systems are provided for adaptive scan control. In one embodiment, a method includes, upon an injection of a contrast agent, initiating a contrast scan of a subject according to a fallback scan prescription, processing acquired projection data of an anatomical region of interest (ROI) of the subject to measure a contrast signal of the contrast agent, identifying a peak in the contrast signal within a predetermined time frame, if the peak in the contrast signal is not identified within the predetermined time frame, updating the fallback scan prescription to generate an adapted scan prescription for the contrast scan based on the contrast signal, and performing a remainder of the contrast scan according to the adapted scan prescription, and if the peak in the contrast signal is not identified within the predetermined time frame, continuing the remainder of the contrast scan according to the fallback scan prescription.

19 Claims, 7 Drawing Sheets

(51) Int. Cl.
*G06T 7/00* (2017.01)
*G06N 20/00* (2019.01)

(52) U.S. Cl.
CPC ........... G06N 20/00 (2019.01); G06T 7/0012 (2013.01); *G06T 2207/10072* (2013.01); *G06T 2207/20084* (2013.01); *G06T 2207/20104* (2013.01)

(58) Field of Classification Search
USPC ......... 382/286–291, 305; 378/4, 21, 15, 108
See application file for complete search history.

(56) References Cited

U.S. PATENT DOCUMENTS

| | | | |
|---|---|---|---|
| 6,236,706 B1* | 5/2001 | Hsieh | A61B 6/504 378/15 |
| 6,256,368 B1 | 7/2001 | Hsieh et al. | |
| 6,891,918 B2 | 5/2005 | Drummond et al. | |
| 7,145,982 B2* | 12/2006 | Ikeda | A61B 6/488 378/108 |
| 7,983,460 B2 | 7/2011 | Licato et al. | |
| 9,327,143 B2 | 5/2016 | Gillece et al. | |
| 9,486,176 B2* | 11/2016 | Goyal | A61B 6/032 |
| 9,517,042 B2 | 12/2016 | Hsieh et al. | |
| 9,622,717 B2 | 4/2017 | Londt et al. | |
| 10,349,909 B2 | 7/2019 | Okerlund et al. | |
| 2017/0086772 A1* | 3/2017 | Vaz | A61B 6/5217 |
| 2017/0209113 A1* | 7/2017 | Jackson | A61B 5/024 |
| 2018/0049714 A1 | 2/2018 | Nett | |
| 2019/0231288 A1 | 8/2019 | Profio et al. | |

OTHER PUBLICATIONS

Hinzpeter, R. et al., "CT Angiography of the Aorta: Contrast Timing by Using a Fixed versus a Patient-specific Trigger Delay," University of Zurich Open Repository and Archive Website, Available Online at https://www.zora.uzh.ch/id/eprint/170529/1/radiol.2019182223.pdf, Available as Early as May 2019, 10 pages.

Lewis, C. et al., "Methods and Sytems for Protocol Management," U.S. Appl. No. 16/553,028, filed Aug. 27, 2019, 59 pages.

Vaz, M. et al., "Methods and Systems for Timing a Second Contrast Bolus," U.S. Appl. No. 16/672,261, filed Nov. 1, 2019, 84 pages.

Vaz, M. et al., "Methods and Systems for an Adaptive Multi-Phase Angiography Scan," U.S. Appl. No. 16/672,281, filed Nov. 1, 2019, 85 pages.

Vaz, M. et al., "Methods and Systems for an Adaptive Five-Zone Perfusion Scan," U.S. Appl. No. 16/672,314, filed Nov. 1, 2019, 85 pages.

Vaz, M. et al., "Methods and Systems for a Single-Bolus Angiography and Perfusion Scan," U.S. Appl. No. 16/672,336, filed Nov. 1, 2019, 85 pages.

Vaz, M. et al., "Methods and Systems for an Adaptive Four-Zone Perfusion Scan," U.S. Appl. No. 16/672,350, filed Nov. 1, 2019, 85 pages.

* cited by examiner under the US 11,452,490 B2

METHODS AND SYSTEMS FOR AN ADAPTIVE PERFUSION SCAN

FIELD

Embodiments of the subject matter disclosed herein relate to non-invasive diagnostic imaging, and more particularly, to real-time adaptive contrast imaging.

BACKGROUND

Non-invasive imaging technologies allow images of the internal structures of a patient or object to be obtained without performing an invasive procedure on the patient or object. In particular, technologies such as computed tomography (CT) use various physical principles, such as the differential transmission of x-rays through the target volume, to acquire image data and to construct tomographic images (e.g., three-dimensional representations of the interior of the human body or of other imaged structures).

For emergency room (ER) stroke management, time is critical to determine a proper course of treatment. For every minute a large vessel ischemic stroke is untreated, the average patient loses 1.9 million neurons. For each hour in which a treatment fails, the patient loses as many neurons as it does in almost 3.6 years of normal aging. Current standards of care typically include a CT perfusion (CTP) study in order to diagnose patient condition and guide treatment decisions. Prior to performing the CTP study, typical methods first perform a timing bolus scan, wherein a small contrast bolus is administered to a patient and subsequent contrast levels within the patient are monitored to generate a CTP scan prescription personalized to the patient. However, the timing bolus scan alone takes five minutes, thus delaying diagnosis and treatment.

BRIEF DESCRIPTION

In one embodiment, a method includes, upon an injection of a contrast agent, initiating a contrast scan of a subject according to a fallback scan prescription, processing acquired projection data of an anatomical region of interest (ROI) of the subject to measure a contrast signal of the contrast agent, identifying a peak in the contrast signal within a predetermined time frame, if the peak is identified within the predetermined time frame, updating the fallback scan prescription to generate an adapted scan prescription for the contrast scan based on the contrast signal, and performing a remainder of the contrast scan according to the adapted scan prescription, and if the peak in the contrast signal is not identified within the predetermined time frame, continuing the remainder of the contrast scan according to the fallback scan prescription.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present disclosure will be better understood from reading the following description of non-limiting embodiments, with reference to the attached drawings, wherein below.

DETAILED DESCRIPTION

Figure 1:
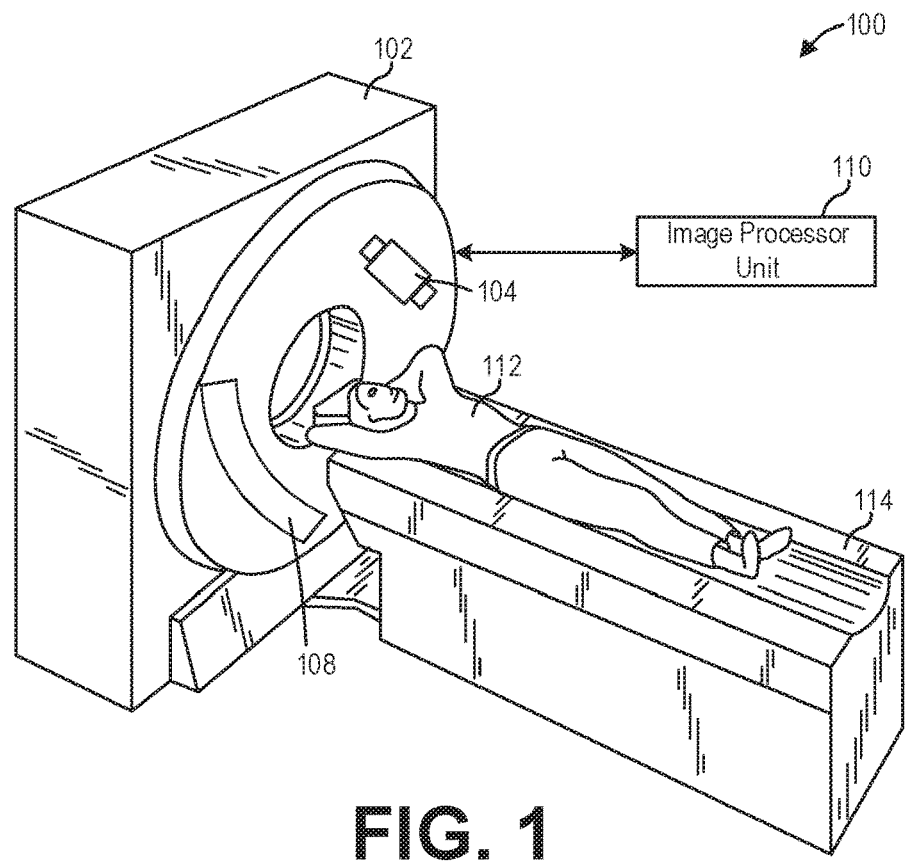
FIG. 1 shows a pictorial view of an imaging system, according to an embodiment.

Some diagnostic imaging protocols, such as protocols to diagnose acute stroke in a patient, include one or more contrast scans, where a contrast agent is administered to the patient prior to the diagnostic imaging scan. Example contrast scans include a computed tomography (CT) angiography (CTA) scan and a CT perfusion (CTP) scan. CTP scans, when used during acute stroke care, may be used by clinicians as a tool to decide if a particular patient will benefit from endovascular thrombectomy. Due to the time sensitive nature of acute stroke care and the scan and reconstruction duration of a CTP scan, the CTP scan may be performed as soon as a patient arrives at a medical facility, before patient information and any recent patient hemodynamic information is available. Thus, under certain clinical situations, it may not be practical to perform a timing bolus of contrast agent to obtain the patient hemodynamic/contrast agent response information.

Thus, as will be described in more detail below, a personalized, adaptive CTP scan may be performed when no prior knowledge of the patient's contrast agent response is available. The adaptive CTP scan described herein may adjust aspects of the scan parameters (e.g., temporal sampling rate) at one or more time points (referred to as zone transitions) that are identified based on the patient's individual contrast agent kinetics, such as the amount of time from contrast agent injection until various inflection points/time points of interest on the patient's arterial inflow function (AIF) curve and venous outflow function (VOF) curve, including but not limited to the venous peak and venous return to baseline. To determine the patient's individual contrast agent kinetics, a contrast agent signal may be measured during an initial portion of the CTP scan, which may comprise a measured contrast level in a monitoring region of the patient (e.g., a brain of the patient). This contrast agent signal may be entered as input to a machine learning (ML) model that may output an estimated AIF curve and an estimated VOF curve (and/or time points of interest from the AIF and VOF curves, such as an arterial peak, a venous peak, and/or a venous return to baseline). Based on the output of the ML model, one or more zone transitions may be identified and adjustments to the scan parameters (e.g., temporal sampling rate) may be made at the zone transitions. In doing so, patient x-ray radiation dose may be reduced, a reconstruction computation load may be reduced, and/or a scan duration may be shortened while still acquiring high quality diagnostic images to support patient diagnosis.

However, in some patients, it may be challenging to identify the estimated AIF curve and the estimated VOF curve (and/or time points of interest from the AIF and VOF curves), as some patients may exhibit contrast agent kinetics that cannot be associated (e.g., by the ML model) with specific AIF and/or VOF curves in a time frame under which such protocol adaptation may be beneficial. Thus, the scan prescription described herein may start out as a fallback, worst case scenario scan prescription that may overscan the patients during an initial portion of the CTP scan protocol, but that may ensure high quality diagnostic images for all patients even if the estimated contrast enhancement curves cannot be determined. Then, if the contrast enhancement curves can be estimated, the fallback scan prescription may be adapted on the fly, as discussed above.

Figure 2:
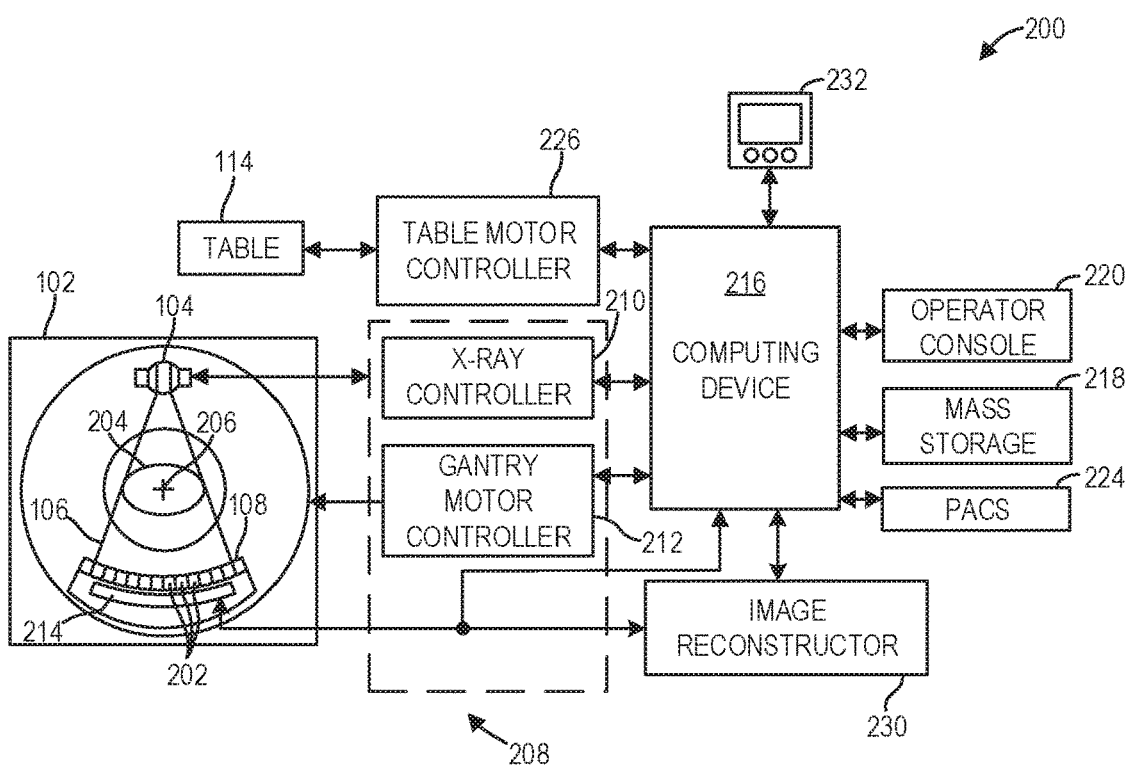
FIG. 2 shows a block schematic diagram of an exemplary imaging system, according to an embodiment.
Figure 3:
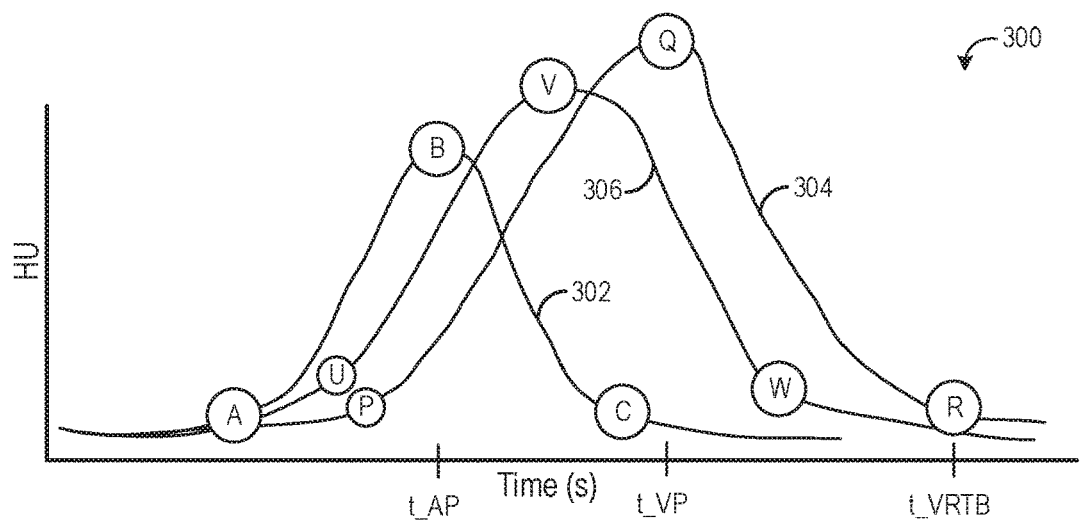
FIG. 3 shows a graph illustrating an example arterial inflow function (AIF) curve, an example a venous outflow function (VOF) curve, and an example tissue uptake curve (TUC) generated during a contrast scan.
Figure 4:
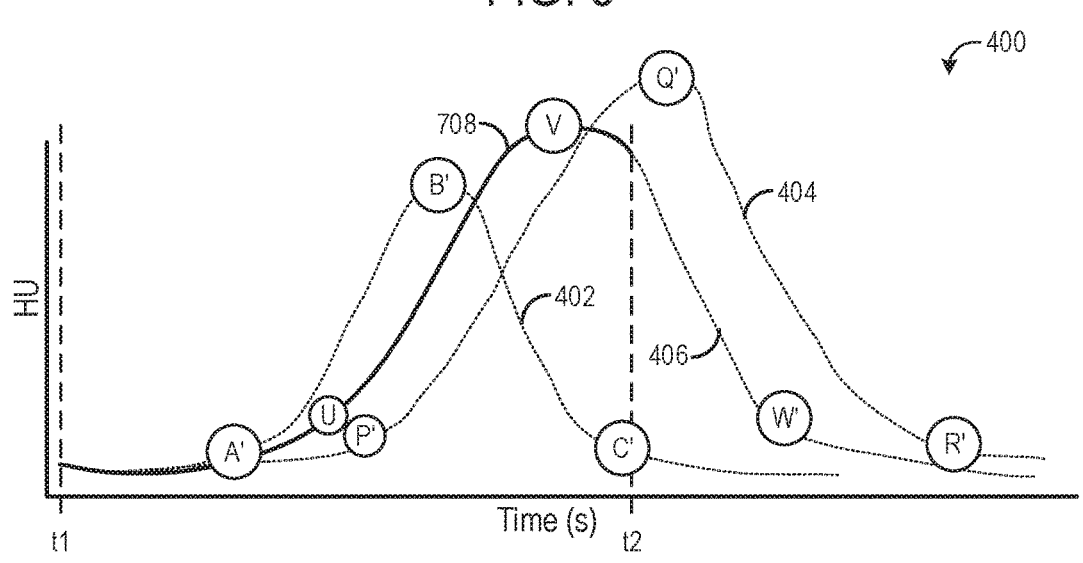
FIG. 4 shows a graph illustrating an estimated AIF curve, an estimated VOF curve, and an estimated TUC generated according to an embodiment of the disclosure.
Figure 5:
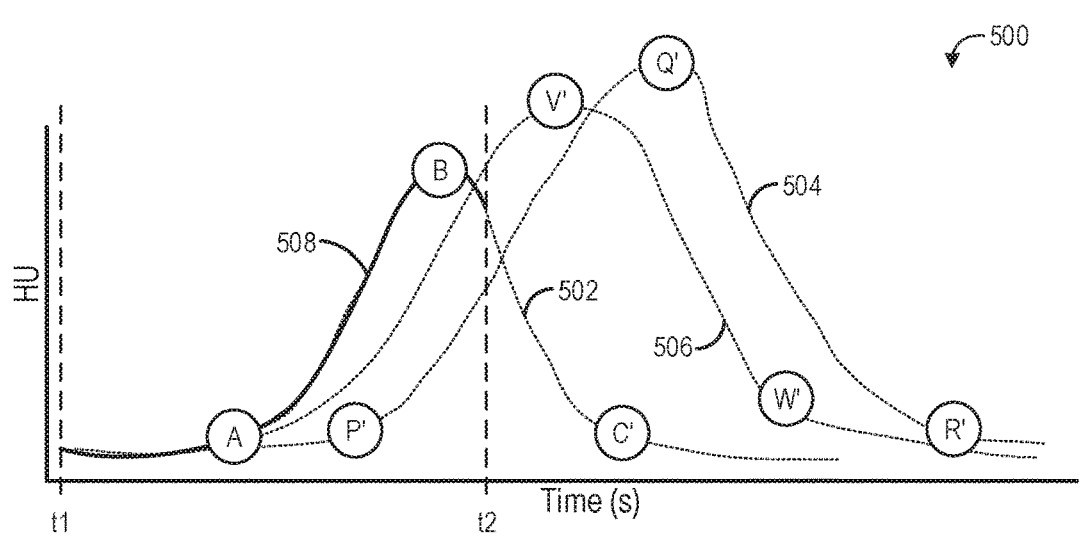
FIG. 5 shows a graph illustrating an estimated AIF curve, an estimated VOF curve, and an estimated TUC generated according to another embodiment of the disclosure.
Figure 7:
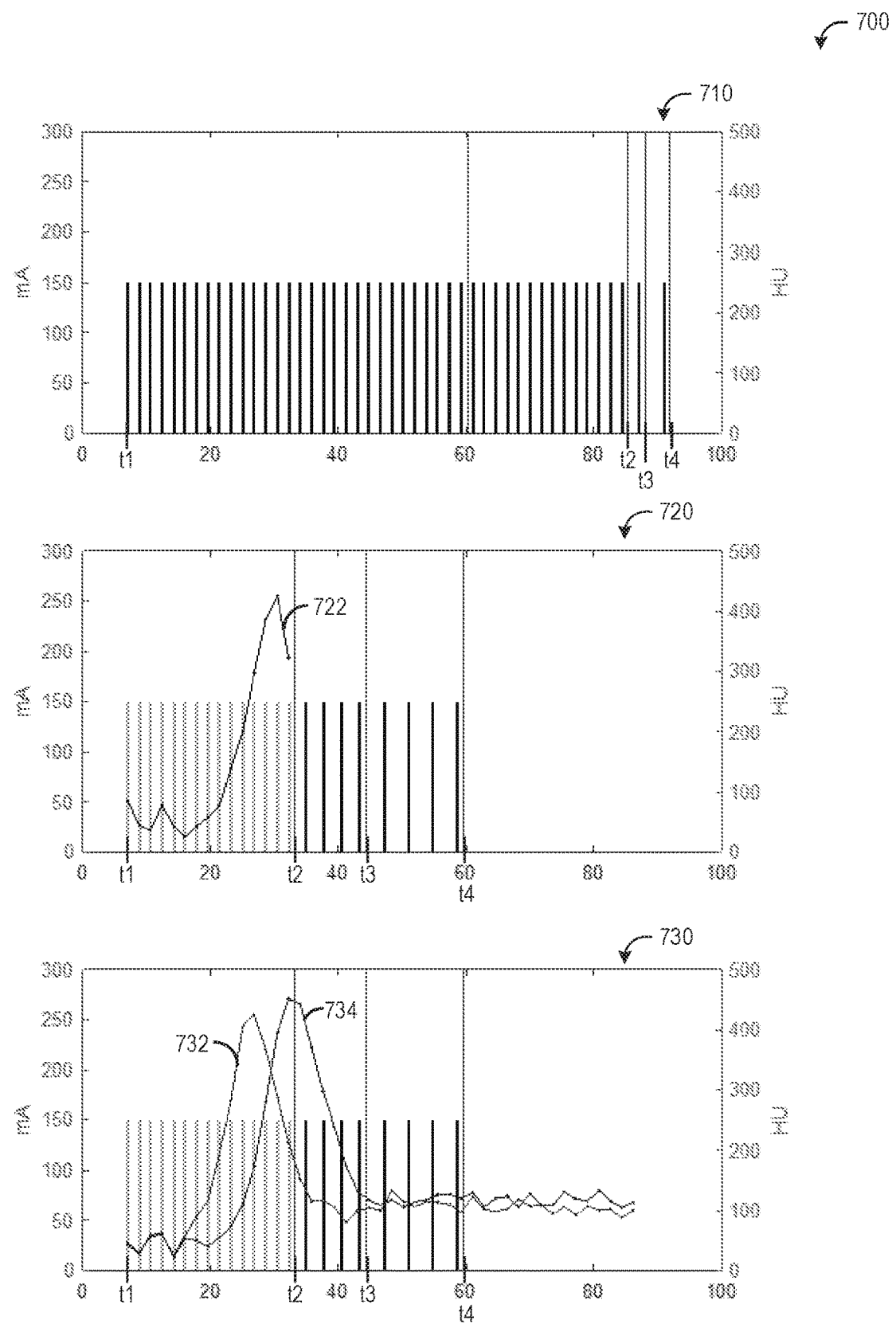
FIG. 7 is a set of graphs depicting a fallback perfusion scan prescription and an adapted perfusion scan prescription, the adapted perfusion scan prescription adapted based on perfusion kinetics determined for a first patient, according to the method of FIG. 6.
Figure 8:
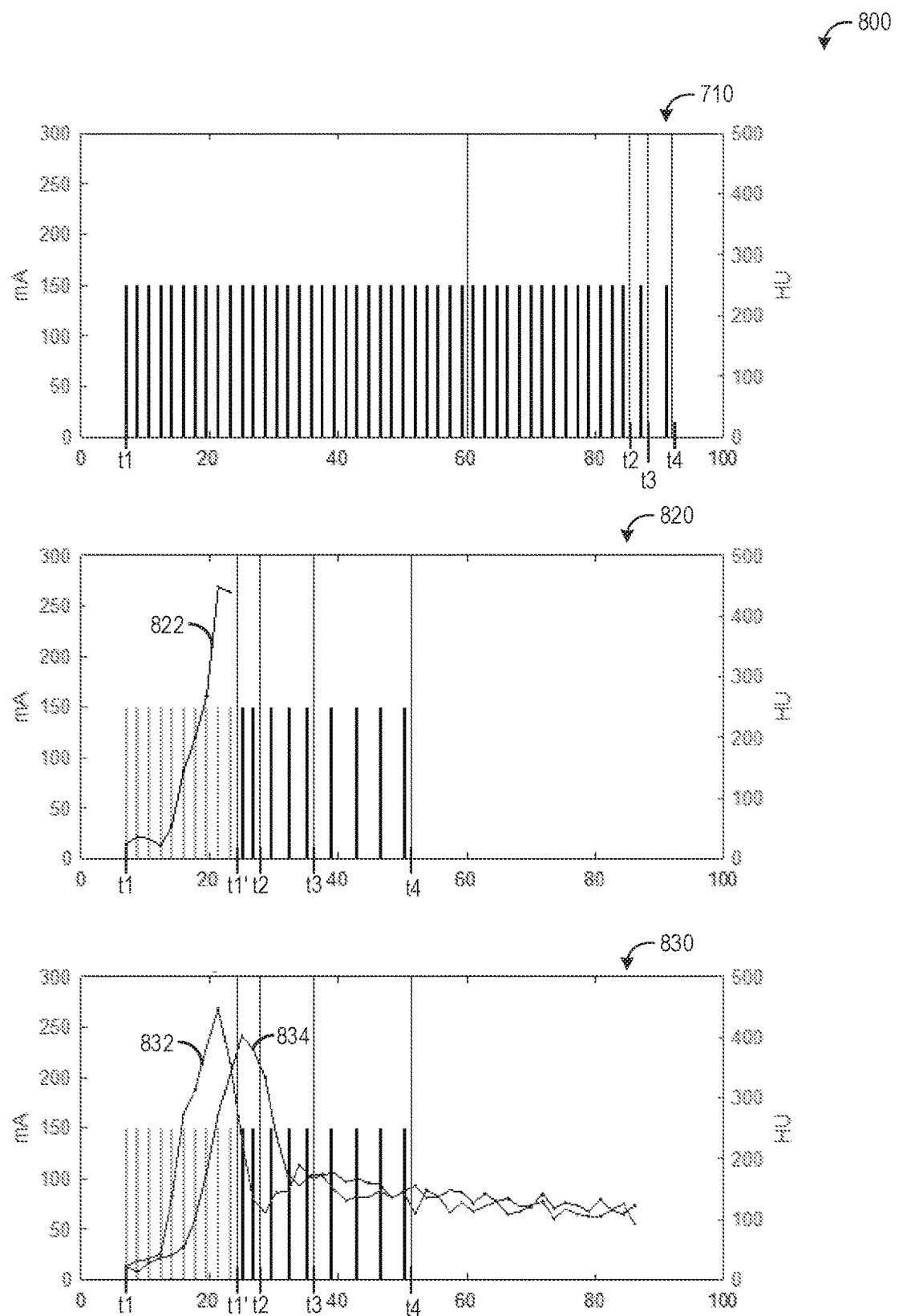
FIG. 8 is a set of graphs depicting a fallback perfusion scan prescription and an adapted perfusion scan prescription, the adapted perfusion scan prescription adapted based on perfusion kinetics determined for a second patient, according to the method of FIG. 6.
Figure 9:
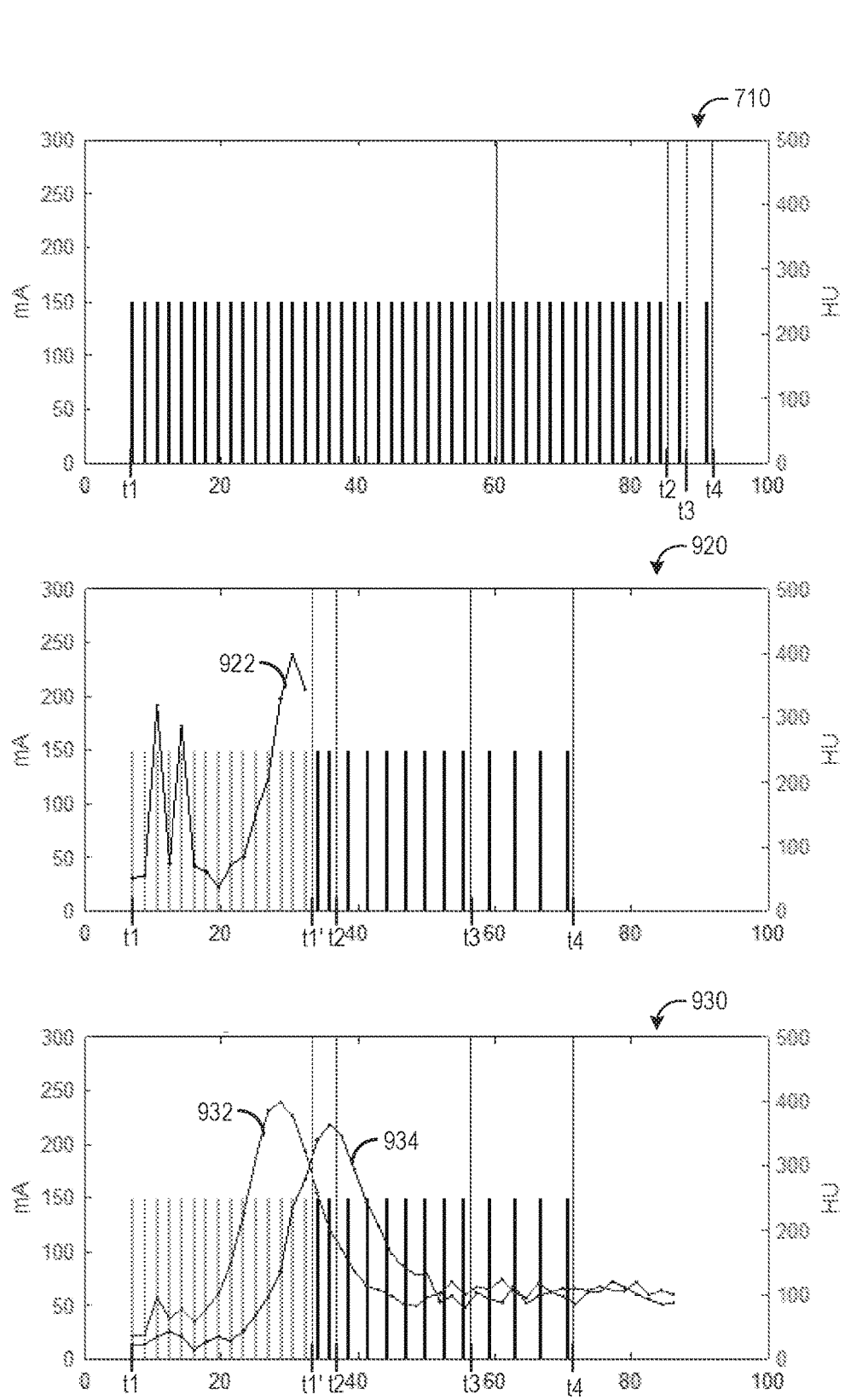
FIG. 9 is a set of graphs depicting a fallback perfusion scan prescription and an adapted perfusion scan prescription, the adapted perfusion scan prescription adapted based on perfusion kinetics determined for a third patient, according to the method of FIG. 6.
Figure 10:
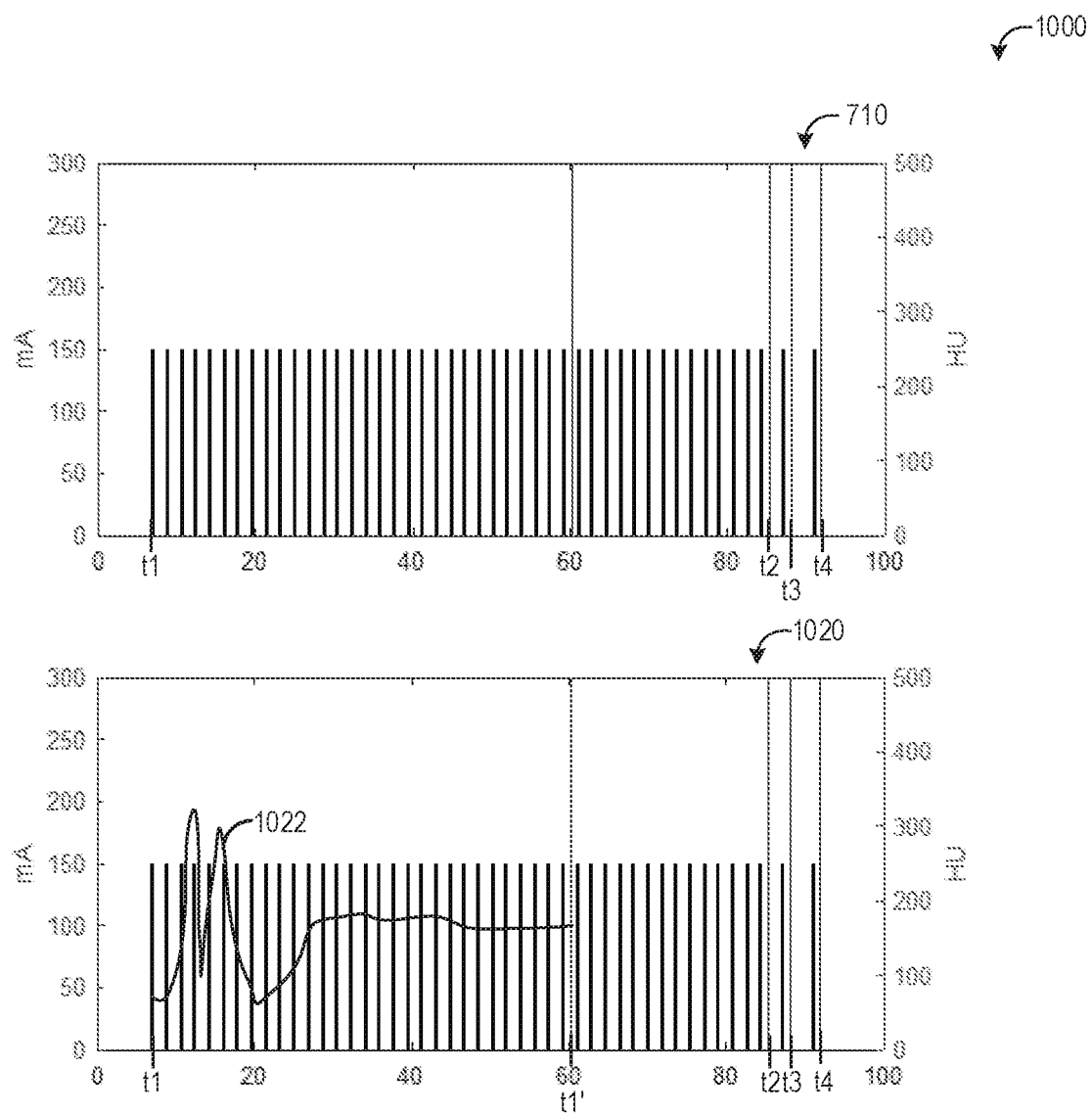
FIG. 10 is a set of graphs illustrating a fallback perfusion scan prescription and how the fallback perfusion scan prescription is maintained for a fourth patient, as the perfusion kinetics are not identifiable for the fourth patient, according to the method of FIG. 6.

An example of a computed tomography (CT) imaging system that may be used to perform the contrast scans in accordance with the present techniques is provided in FIGS. 1 and 2. As described above, the adaptation of the contrast scans may be dependent on the AIF and/or VOF curves of the contrast agent, which vary from patient to patient. FIG. 3 shows example AIF and VOF curves for a patient. A portion of the AIF curve may be directly measured prior to a first contrast scan commencing or during the first portion of the first contrast scan, and this portion may be used as input to a model to estimate the remaining AIF curve and the VOF curve for the patient, as shown in FIG. 5. As another example, rather than measuring the AIF, tissue uptake of the contrast agent may be measured for a duration, and this measured portion of the tissue uptake curve (TUC) may be entered into a model to estimate the AIF and VOF curves, as shown in FIG. 4. Adaptive scan control may be carried out according to the method of FIG. 6, where a fallback scan prescription may be followed during a CTP scan, and this fallback scan prescription may be adapted based on individual patient contrast agent kinetics, as determined from the AIF curve or TUC, if such kinetics can be determined. FIGS. 7-9 show example scan prescriptions adaptations for different patients, while FIG. 10 shows an example patient where the fallback scan prescription is not adapted.

Though a CT system is described by way of example, it should be understood that the present techniques may also be useful when applied to images acquired using other imaging modalities, such as x-ray imaging systems, magnetic resonance imaging (MRI) systems, positron emission tomography (PET) imaging systems, single-photon emission computed tomography (SPECT) imaging systems, ultrasound imaging systems, and combinations thereof (e.g., multi-modality imaging systems, such as PET/CT, PET/MR or SPECT/CT imaging systems). The present discussion of a CT imaging modality is provided merely as an example of one suitable imaging modality. Further, while the present techniques may be discussed herein with respect to head/neck scans such as acute stroke scan protocols, the present techniques may be applied during other contrast scan protocols, such as cardiac scans, liver scans, etc.

FIG. 1 illustrates an exemplary CT system 100 configured for CT imaging. Particularly, the CT system 100 is configured to image a subject 112 such as a patient, an inanimate object, one or more manufactured parts, and/or foreign objects such as dental implants, stents, and/or contrast agents present within the body. In one embodiment, the CT system 100 includes a gantry 102, which in turn, may further include at least one x-ray source 104 configured to project a beam of x-ray radiation 106 (see FIG. 2) for use in imaging the subject 112 laying on a table 114. Specifically, the x-ray source 104 is configured to project the x-ray radiation beams 106 towards a detector array 108 positioned on the opposite side of the gantry 102. Although FIG. 1 depicts only a single x-ray source 104, in certain embodiments, multiple x-ray sources and detectors may be employed to project a plurality of x-ray radiation beams 106 for acquiring projection data at different energy levels corresponding to the patient. In some embodiments, the x-ray source 104 may enable dual-energy gemstone spectral imaging (GSI) by rapid peak kilovoltage (kVp) switching. In some embodiments, the x-ray detector employed is a photon-counting detector which is capable of differentiating x-ray photons of different energies. In other embodiments, two sets of x-ray sources and detectors are used to generate dual-energy projections, with one set at low-kVp and the other at high-kVp. It should thus be appreciated that the methods described herein may be implemented with single energy acquisition techniques as well as dual energy acquisition techniques.

In certain embodiments, the CT system 100 further includes an image processor unit 110 configured to reconstruct images of a target volume of the subject 112 using an iterative or analytic image reconstruction method. For example, the image processor unit 110 may use an analytic image reconstruction approach such as filtered back projection (FBP) to reconstruct images of a target volume of the patient. As another example, the image processor unit 110 may use an iterative image reconstruction approach such as advanced statistical iterative reconstruction (ASIR), conjugate gradient (CG), maximum likelihood expectation maximization (MLEM), model-based iterative reconstruction (MBIR), and so on to reconstruct images of a target volume of the subject 112. As described further herein, in some examples the image processor unit 110 may use both an analytic image reconstruction approach such as FBP in addition to an iterative image reconstruction approach.

In some CT imaging system configurations, an x-ray source projects a cone-shaped x-ray radiation beam which is collimated to lie within an X-Y-Z plane of a Cartesian coordinate system and generally referred to as an "imaging plane." The x-ray radiation beam passes through an object being imaged, such as the patient or subject. The x-ray radiation beam, after being attenuated by the object, impinges upon an array of detector elements. The intensity of the attenuated x-ray radiation beam received at the detector array is dependent upon the attenuation of a radiation beam by the object. Each detector element of the array produces a separate electrical signal that is a measurement of the x-ray beam attenuation at the detector location. The attenuation measurements from all the detector elements are acquired separately to produce a transmission profile.

In some CT systems, the x-ray source and the detector array are rotated with a gantry within the imaging plane and around the object to be imaged such that an angle at which the radiation beam intersects the object constantly changes. A group of x-ray radiation attenuation measurements, e.g., projection data, from the detector array at one gantry angle is referred to as a "view." A "scan" of the object includes a set of views made at different gantry angles, or view angles, during one revolution of the x-ray source and detector. It is contemplated that the benefits of the methods described herein accrue to medical imaging modalities other than CT, so as used herein the term "view" is not limited to the use as described above with respect to projection data from one gantry angle. The term "view" is used to mean one data acquisition whenever there are multiple data acquisitions from different angles, whether from a CT, positron emission tomography (PET), or single-photon emission CT (SPECT) acquisition, and/or any other modality including modalities yet to be developed as well as combinations thereof in fused embodiments.

The projection data is processed to reconstruct an image that corresponds to a two-dimensional slice taken through the object or, in some examples where the projection data includes multiple views or scans, a three-dimensional rendering of the object. One method for reconstructing an image from a set of projection data is referred to in the art as the filtered back projection technique. Transmission and emission tomography reconstruction techniques also include statistical iterative methods such as maximum likelihood expectation maximization (MLEM) and ordered-subsets expectation-reconstruction techniques as well as iterative reconstruction techniques. This process converts the attenuation measurements from a scan into integers called "CT numbers" or "Hounsfield units," which are used to control the brightness of a corresponding pixel on a display device.

To reduce the total scan time, a "helical" scan may be performed. To perform a "helical" scan, the patient is moved while the data for the prescribed number of slices is acquired. Such a system generates a single helix from a cone beam helical scan. The helix mapped out by the cone beam yields projection data from which images in each prescribed slice may be reconstructed.

As used herein, the phrase "reconstructing an image" is not intended to exclude embodiments of the present invention in which data representing an image is generated but a viewable image is not. Therefore, as used herein, the term "image" broadly refers to both viewable images and data representing a viewable image. However, many embodiments generate (or are configured to generate) at least one viewable image.

FIG. 2 illustrates an exemplary imaging system 200 similar to the CT system 100 of FIG. 1. In accordance with aspects of the present disclosure, the imaging system 200 is configured for imaging a subject 204 (e.g., the subject 112 of FIG. 1). In one embodiment, the imaging system 200 includes the detector array 108 (see FIG. 1). The detector array 108 further includes a plurality of detector elements 202 that together sense the x-ray radiation beam 106 (see FIG. 2) that pass through the subject 204 (such as a patient) to acquire corresponding projection data. Accordingly, in one embodiment, the detector array 108 is fabricated in a multi-slice configuration including the plurality of rows of cells or detector elements 202. In such a configuration, one or more additional rows of the detector elements 202 are arranged in a parallel configuration for acquiring the projection data.

In certain embodiments, the imaging system 200 is configured to traverse different angular positions around the subject 204 for acquiring desired projection data. Accordingly, the gantry 102 and the components mounted thereon may be configured to rotate about a center of rotation 206 for acquiring the projection data, for example, at different energy levels. Alternatively, in embodiments where a projection angle relative to the subject 204 varies as a function of time, the mounted components may be configured to move along a general curve rather than along a segment of a circle.

As the x-ray source 104 and the detector array 108 rotate, the detector array 108 collects data of the attenuated x-ray beams. The data collected by the detector array 108 undergoes pre-processing and calibration to condition the data to represent the line integrals of the attenuation coefficients of the scanned subject 204. The processed data are commonly called projections.

In some examples, the individual detectors or detector elements 202 of the detector array 108 may include photon-counting detectors which register the interactions of individual photons into one or more energy bins. It should be appreciated that the methods described herein may also be implemented with energy-integrating detectors.

The acquired sets of projection data may be used for basis material decomposition (BMD). During BMD, the measured projections are converted to a set of material-density projections. The material-density projections may be reconstructed to form a pair or a set of material-density map or image of each respective basis material, such as bone, soft tissue, and/or contrast agent maps. The density maps or images may be, in turn, associated to form a volume rendering of the basis material, for example, bone, soft tissue, and/or contrast agent, in the imaged volume.

Once reconstructed, the basis material image produced by the imaging system 200 reveals internal features of the subject 204, expressed in the densities of two basis materials. The density image may be displayed to show these features. In traditional approaches to diagnosis of medical conditions, such as disease states, and more generally of medical events, a radiologist or physician would consider a hard copy or display of the density image to discern characteristic features of interest. Such features might include lesions, sizes and shapes of particular anatomies or organs, and other features that would be discernable in the image based upon the skill and knowledge of the individual practitioner.

In one embodiment, the imaging system 200 includes a control mechanism 208 to control movement of the components such as rotation of the gantry 102 and the operation of the x-ray source 104. In certain embodiments, the control mechanism 208 further includes an x-ray controller 210 configured to provide power and timing signals to the x-ray source 104. Additionally, the control mechanism 208 includes a gantry motor controller 212 configured to control a rotational speed and/or position of the gantry 102 based on imaging requirements.

In certain embodiments, the control mechanism 208 further includes a data acquisition system (DAS) 214 configured to sample analog data received from the detector elements 202 and convert the analog data to digital signals for subsequent processing. The DAS 214 may be further configured to selectively aggregate analog data from a subset of the detector elements 202 into so-called macrodetectors, as described further herein. The data sampled and digitized by the DAS 214 is transmitted to a computer or computing device 216. In one example, the computing device 216 stores the data in a storage device or mass storage 218. The storage device 218, for example, may include a hard disk drive, a floppy disk drive, a compact disk-read/write (CD-R/W) drive, a Digital Versatile Disc (DVD) drive, a flash drive, and/or a solid-state storage drive.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters via an operator console 220 operatively coupled to the computing device 216. The operator console 220 may include a keyboard (not shown) or a touchscreen to allow the operator to specify the commands and/or scanning parameters.

Although FIG. 2 illustrates only one operator console 220, more than one operator console may be coupled to the imaging system 200, for example, for inputting or outputting system parameters, requesting examinations, plotting data, and/or viewing images. Further, in certain embodiments, the imaging system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks, wireless telephone networks, wireless local area networks, wired local area networks, wireless wide area networks, wired wide area networks, etc.

In one embodiment, for example, the imaging system 200 either includes, or is coupled to, a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a table 114 which may be a motorized table. Specifically, the table motor controller 226 may move the table 114 for appropriately positioning the subject 204 in the gantry 102 for acquiring projection data corresponding to the target volume of the subject 204.

As previously noted, the DAS 214 samples and digitizes the projection data acquired by the detector elements 202. Subsequently, an image reconstructor 230 uses the sampled and digitized x-ray data to perform high-speed reconstruction. Although FIG. 2 illustrates the image reconstructor 230 as a separate entity, in certain embodiments, the image reconstructor 230 may form part of the computing device 216. Alternatively, the image reconstructor 230 may be absent from the imaging system 200 and instead the computing device 216 may perform one or more functions of the image reconstructor 230. Moreover, the image reconstructor 230 may be located locally or remotely, and may be operatively connected to the imaging system 200 using a wired or wireless network. Particularly, one exemplary embodiment may use computing resources in a "cloud" network cluster for the image reconstructor 230.

In one embodiment, the image reconstructor 230 stores the images reconstructed in the storage device 218. Alternatively, the image reconstructor 230 may transmit the reconstructed images to the computing device 216 for generating useful patient information for diagnosis and evaluation. In certain embodiments, the computing device 216 may transmit the reconstructed images and/or the patient information to a display or display device 232 communicatively coupled to the computing device 216 and/or the image reconstructor 230. In some embodiments, the reconstructed images may be transmitted from the computing device 216 or the image reconstructor 230 to the storage device 218 for short-term or long-term storage.

The various methods and processes (such as the method described below with reference to FIG. 6) described further herein may be stored as executable instructions in non-transitory memory on a computing device (or controller) in imaging system 200. In an embodiment, computing device 216 may include the instructions in non-transitory memory, and may apply the methods described herein, at least in part, to measure the AIF or TUC signals from a plurality of reconstructed images after receiving the reconstructed images from image reconstructor 230. The computing device 216 may then enter the AIF or TUC signal to a model to estimate the AIF and VOF curves, as described below, in order to optimally plan personalized contrast scan prescriptions, as described below. In other embodiments, image reconstructor 230 may include such executable instructions in non-transitory memory, and may apply the methods described herein to adaptively plan and control contrast scans. In yet another embodiment, the methods and processes described herein may be distributed across image reconstructor 230 and computing device 216.

In one embodiment, the display 232 allows the operator to evaluate the imaged anatomy, view measured and/or estimated AIF and VOF curves, trigger aspects of the contrast scans, and the like. The display 232 may also allow the operator to select a region of interest (ROI) and/or request patient information, for example, via a graphical user interface (GUI) for a subsequent scan or processing.

FIG. 3 shows a graph 300 depicting an example AIF curve 302, an example VOF curve 304, and an example tissue uptake curve (TUC) 306 each plotted as HU as a function of time. AIF curve 302 represents the change in the arterial inflow of a contrast agent over time for a patient, and VOF curve 304 represents the change in the venous outflow of the contrast agent over time for the patient. The AIF curve 302 may be measured at an arterial ROI, such as anterior cerebral artery or internal carotid artery, and may include a measurement of signal intensity in the arterial ROI relative to a baseline intensity (e.g., in the arterial ROI prior to contrast injection). The VOF curve 304 may be measured at a venous ROI, such as the superior sagittal sinus, and may include a measurement of the signal intensity in the venous ROI relative to a baseline intensity (e.g., in the venous ROI prior to contrast injection). TUC 306 may represent the change in detected contrast agent in a tissue of interest, as the contrast agent is taken up by the tissue and then depleted from the tissue. To measure the TUC, tissue of interest (e.g., the brain parenchyma) may be segmented in each of a plurality of reconstructed images, and the overall or average HU of in the segmented region of each of the plurality of reconstructed images may be determined relative to a baseline level and plotted over time. Additional details regarding the tissue segmentation and TUC signal measurement are provided below with respect to FIG. 6.

The AIF curve 302 may include an arterial ascent knee at approximately point A on the curve, an arterial peak at point B on the curve, and an arterial descent knee at approximately point C on the curve. The amount of time from contrast injection until the arterial peak is reached may be the time to arterial peak, indicated as t_AP on FIG. 3. The VOF curve 304 may include a venous ascent knee at approximately point P on the curve, a venous peak at point Q on the curve, and a venous descent knee at approximately point R on the curve. The amount of time from contrast injection until the venous peak is reached may be the time to venous peak, indicated as t_VP on FIG. 3. The amount of time from contrast injection until the venous return to baseline (VRTB) is reached may be the time to VRTB, indicated as t_VRTB on FIG. 3. TUC 306 may include an ascent knee at approximately point U on the curve, a TUC peak at point V on the curve, and a descent knee at approximately point W on the curve.

The amount of time it may take to reach the points marked on the curves in FIG. 3 may vary from patient to patient, as body weight, cardiac function, and other factors may impact the contrast agent inflow and outflow rate. As will be explained in more detail below, certain contrast scan protocols, such as perfusion scans, rely on the AIF and/or VOF curves, and the timing of one or more of the points described above (e.g., the venous peak) may be determined and used as a trigger for adjusting scan parameters. However, some scan protocols are condensed as much as possible so that diagnostic information may learned as quickly as possible in order to facilitate patient care. For example, scan protocols carried out as part of an acute stroke assessment may be designed to be as short as possible, while still collecting the needed diagnostic image information, so that needed patient care may be administered as quickly as possible. Thus, the amount of time needed to completely measure the AIF curve, the VOF curve, and/or the TUC for a patient prior to initiation of the diagnostic scan(s) may delay patient care and negatively impact patient outcomes. Further, when the imaging system includes x-rays directed to the patient (such as the CT system described above with respect to FIGS. 1-2), it may be desired to minimize patient radiation exposure. Thus, acute stroke and other contrast scan protocols may include a short measurement of the AIF curve, for example, and scan protocol adjustments may be based on this limited information and/or certain aspects of the scan protocols may be carried out with fixed timing that is not changed from patient to patient. While such protocols may be suitable for ensuring that most scans generate sufficient diagnostic information, some scans may result in images that are not suitable for diagnosing the patient condition or may lead to unnecessary radiation exposure.

Thus, prior to or during the beginning of a contrast scan, a small segment of the TUC or the AIF curve may be measured and this TUC or AIF curve measurement (referred to as a TUC signal or an AIF signal) may be used to estimate the remainder of the TUC, the remainder of the AIF curve, and/or the VOF curve. To ensure an accurate estimation, a machine learning model may be deployed that is trained using a plurality of different TUC or AIF signals measured from different patients along with associated full AIF, TUC, and VOF curves (or associated points of interest on the AIF, TUC, and VOF curves, such as the points labeled on FIG. 3 and described above). The measured TUC signal or AIF signal may be entered into the trained and validated machine learning model, and the model may output an estimated AIF curve, estimated TUC, and estimated VOF curve, or the model may output the time to one or more significant points of the TUC and AIF and VOF curves, such as the time to arterial peak, the time to venous peak, and the time to venous return to baseline. The scan protocols may then be adapted on the fly on a patient by patient basis using the estimated TUC and AIF and VOF curves and/or estimated time points of the TUC and AIF and VOF curves.

FIG. 4 shows a graph 400 depicting an estimated AIF curve 402, an estimated VOF curve 404, and an estimated TUC 406, each estimated according to a TUC estimation method. The tissue uptake of a contrast agent (e.g., of a contrast bolus) may be monitored and used to set parameters for the in-flight contrast scan. As shown, a first segment 408 of the TUC is measured as described above (e.g., a change in HU level relative to a baseline level measured across a plurality of images). The first segment 408 may commence when the contrast bolus is administered (e.g., at time t1 in FIG. 4) and end after the TUC peak (e.g., at time t2 in FIG. 4). The first segment 408 may be entered into a model to estimate the remaining portion of the estimated TUC 406 and all of the estimated AIF curve 402 and VOF curve 404. As a result, time points U and V are measured while time points A', B', C', P', Q', and R' are estimated.

FIG. 5 shows a graph 500 depicting an estimated AIF curve 502, an estimated VOF curve 504, and an estimated TUC 506 each estimated according to an AIF estimation method. The inflow of the contrast agent of the contrast bolus may be monitored and used to set parameters for the contrast scan. As shown, a first segment 508 of the AIF curve is measured as described above (e.g., in a ROI based on change in HU level relative to a baseline level). The first segment 508 may commence when the contrast bolus is administered (e.g., at time t1 in FIG. 5) and end after the arterial peak (e.g., at time t2 in FIG. 5). The first segment 508 may be entered into a model to estimate the remaining portion of the estimated AIF curve 502, the TUC 506, and/or all of the estimated VOF curve 504. As a result, time points A and B are measured while time points P', V', C', Q', W', and R' are estimated.

Thus, the TUC and AIF and VOF curves (or selected time points of the TUC and AIF and VOF curves) may be estimated using a relatively short measured segment of the TUC or the AIF curve that is entered into a machine learning model. While the AIF estimation method was described as being based on a single arterial ROI, it is to be understood that multiple arterial ROIs could be measured and combined (e.g., averaged) to measure the AIF curve. Further, the VOF curve could be measured for the same time period as the AIF curve (e.g., from time t1 until the respective time t2) by monitoring a venous ROI, and the measured segment of the VOF curve could be used as input to the model in addition to the measured segment of the AIF curve, which may result in a more robust estimation of the remaining portions of the AIF and VOF curves.

The arterial ROI and venous ROI described above may be positioned at any suitable location where arterial inflow and venous outflow, respectively, of contrast agent may be detectable, and the selection of where to position the arterial ROI and/or venous ROI may depend on the scan protocol (e.g., what anatomy is going to be imaged in the contrast scan). However, some anatomy, such as the brain, may present challenges for arterial or venous ROI placement, as the ability to visualize certain anatomical features may require presence of a contrast agent. Thus, to place an arterial or venous ROI in the head/brain, a separate administration of contrast agent may be needed to even place the ROI, which may make arterial or venous ROI placement in the head unpractical. Thus, the arterial ROI and/or venous ROI may typically be placed in the neck area or another adjacent anatomy, and then the patient may be moved relative to the CT imaging system (e.g., via table movement) to position the head in the proper location for the contrast scan. However, this additional table movement may prolong the duration of the scan session and/or make some adaptive scan protocols unpractical. Thus, some scan protocols may utilize the TUC estimation method in order to determine the various time points of interest/individual patient contrast kinetics. Accordingly, the AIF, TUC, and VOF curves (or selected time points of the AIF, TUC, and VOF curves) may be estimated using a relatively short measured segment of the TUC that is entered into a machine learning model.

A CT perfusion scan (referred to as a CTP scan) may produce diagnostic images showing blood profusion and delivery of blood or blood flow to a tissue of interest, such as a brain. A first example of a typical CTP scan prescription of the head may include a series of acquisitions performed at a single temporal sampling rate, also known as temporal acquisition rate, (e.g., one acquisition each 2 s) for a fixed duration (e.g., 90 s) following injection of a contrast bolus (assuming a prep delay between injection of the contrast bolus and the first acquisition of 5-7 s). In second example of a typical CTP scan prescription of the head, the acquisitions may be carried out at two different temporal sampling rates, for example a first temporal sampling rate (e.g., of one acquisition every 2 s) for a first duration (e.g., of 30 s) and then a second temporal sampling rate (e.g., of one acquisition every 5 s) for a second duration (e.g., of 35 s, for a total of 70 s) following injection of a contrast bolus (assuming a prep delay between injection of the contrast bolus and the first acquisition of 5-7 s). Ideally, a patient would be scanned at a higher temporal sampling rate during contrast enhancement (e.g., during the arterial and venous peaks) and scanning would end soon after the contrast agent returned to baseline. In the first example CTP scan prescription, the majority of patients, regardless of individual AIF and VOF curves, would be scanned such that diagnostic images are obtained, but some patients may be over-scanned. For example, patients with relatively short AIF/VOF peak times may be scanned for a relatively long duration after the contrast agent has returned to baseline, resulting in overly lengthy scan times and unnecessary radiation doses. In the second example CTP scan prescription, some patients (e.g., those with relatively long AIF/VOF peak times, such as older patients or patients with atrial fibrillation) may be under-scanned such that sufficient images as contrast is being washed out are not obtained, resulting in image quality issues (e.g., unreliable penumbra/blood flow quantitation, which may lead to an incorrect decision being made regarding whether the patient should receive an endovascular thrombectomy or other treatment). Thus, with typical CTP protocols, a tradeoff may be made between ensuring high quality images for all patients and increased exam time and corresponding increased radiation dose for some patients.

Thus, according to embodiments disclosed herein, a personalized adaptive CTP scan may be carried out based on the patient-specific contrast signal and output of the machine learning model described above (e.g., based on the estimated VOF curve). The CTP scan prescription may be defined by one or more zone transitions (e.g., from one zone to the next zone), and when these zone transitions are to occur may be estimated using the machine learning model with the measured contrast signal (e.g., measured TUC signal) as input to the machine learning model. The scan prescription for the CTP scan (e.g., the CT system parameters for carrying out the scan) may be dynamically adapted during execution of the CTP scan based on the timing of each zone transition, such that the CTP scan may be carried out in a manner that is optimized for the specific patient. In doing so, total scan time may be reduced, radiation exposure may be lowered, and image quality may be maintained.

However, some patients may have TUCs (or AIF curves, depending on the contrast signal used to adapt the scan prescription) that may have a slow ascent, undetectable peak, or other parameter that may make estimating the various time points discussed herein (e.g., the venous peak and venous return to baseline) in a timely manner challenging. For example, when the TUC signal is entered as input to the ML model, the ML model may utilize the time that the TUC peak occurred as one aspect of the TUC signal that predicts the remaining time points/curves, such as the venous peak and/or venous return to baseline. If a TUC peak is not detectable, the adaptation to the scan prescription may not function as intended. Thus, as described in more detail herein, a fallback scan prescription may be initially executed that is configured to sufficiently scan nearly all patients, where the fallback scan prescription may include, for most of the scan prescription, the highest temporal sampling rate indicated for any aspect of the CTP scan (e.g., the temporal sampling rate indicated for the contrast enhancement segment). Thus, the fallback scan prescription may include a temporal sampling rate that is higher than needed during the beginning portion and ending portion of the CTP scan. During execution of the fallback scan prescription, the TUC signal may be generated and monitored for the TUC peak. If a TUC peak is detected, the TUC signal may be entered as input to the ML model to estimate the remaining time points/curves, and the scan prescription may be adapted on the fly based on the estimated remaining time points/curves (e.g., the temporal sampling rate may be reduced after the contrast enhancement segment of the scan). If a TUC peak is not detected within a predetermined time frame, the fallback scan prescription may be maintained until the scan is complete. In this way, sufficient scanning may be ensured regardless of when, or if, a TUC peak is detected.

Figure 6:
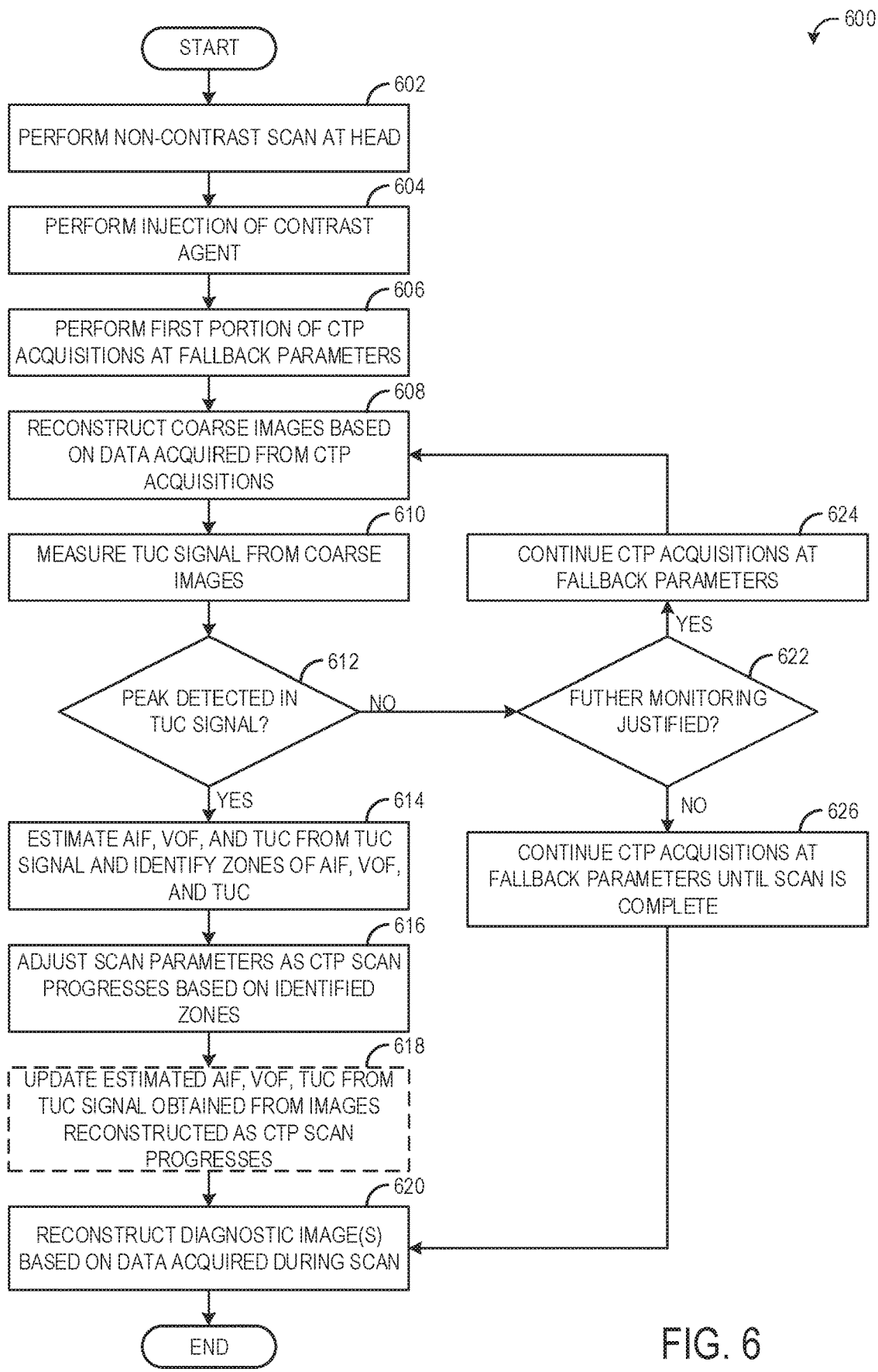
FIG. 6 is a flow chart illustrating a method for performing an adaptive perfusion scan, according to an embodiment of the disclosure.

FIG. 6 shows a flow chart illustrating a method 600 for carrying out a personalized adaptive CTP scan. Method 600 is described with respect to the system and components described above with respect to FIGS. 1-2 but could be carried out with other systems/components without departing from the scope of this disclosure. Method 600 may be carried out according to instructions stored in non-transitory memory of a computing device (e.g., computing device 216 of FIG. 2). Method 600 may include identification of estimated times of transitions between two or more zones of a CTP scan, which may be used to update a scan prescription for carrying out the CTP scan. Thus, method 600 may be performed in response to user selection of a scanning protocol that includes a CTP, such as a stand-alone CTP, a CTA followed by a CTP, a CTP followed by a CTA, a combined CTP and CTA, etc.

At 602, a non-contrast scan is optionally performed. The non-contrast scan may be taken to establish a baseline image for the area to be monitored before delivery of a contrast agent. The baseline image may then be used to align the patient and the region of interest within the imaging device. The non-contrast scan may be of the head in the example method presented herein, but it is to be understood that the non-contrast scan may be performed at another suitable anatomical region depending on the scan protocol. At 604, an injection of contrast agent into the patient is performed.

As a non-limiting example, the contrast agent may comprise iodine. As other examples, the contrast agent may comprise an ionic contrast medium such as meglucamine diatriozoate, or a non-ionic contrast medium such as iopromide or ohexol. The contrast agent may be intravenously injected using either automatic or manual methods. The injection may be a contrast bolus for an in-flight CTP scan and may be the only contrast injection performed for the CTP scan. At 606, a first portion of CTP acquisitions are performed at fallback scan parameters. The fallback scan parameters may include a fast temporal resolution. In one example, the fast temporal resolution of the fallback scan parameters may include a temporal sampling rate of one acquisition each 2 seconds. The fallback scan parameters may further include a predefined x-ray source current and a predefined x-ray source voltage. The temporal sampling rate may also be referred to as a temporal acquisition rate and may include the frequency at which imaging system acquisitions (also referred to as passes) are performed. As used herein, a scan acquisition or pass may refer to a full gantry rotation (e.g., when the brain is being imaged) or a partial gantry rotation (e.g., when the heart is being imaged). In either case, an acquisition or pass may include the amount of gantry rotation that is needed to obtain the desired views for the anatomy/scanning protocol.

At 608, one or more "coarse" images are reconstructed from the data acquired during the CTP acquisitions. The coarse images may be reconstructed using a coarse reconstruction process that has a low computational load and thus may be performed rapidly. Because the images reconstructed at 608 are not diagnostic images but instead are images reconstructed to monitor the tissue uptake of the contrast agent, the coarse reconstruction process may sacrifice diagnostic quality in order to allow the images to be quickly reconstructed. The coarse reconstruction process may include 128×128 slices that are 5 mm thick, and the reconstruction process may take about 1 second per acquisition.

At 610, the TUC signal is measured from the coarse images. Measuring the TUC signal may include segmenting, in each coarse image, a tissue of interest, such as the brain. The segmentation process may include thresholding the image, performing an erosion process on the thresholded image, identifying the largest object, and then performing a dilation process. However, other segmentation processes may be carried out without departing from the scope of this disclosure. Once the tissue of interest has been segmented, the overall or average signal intensity (e.g., pixel brightness) for the segmented region may be determined and compared to a baseline intensity (e.g., of that tissue/segmented region prior to contrast injection). The signal intensity of each coarse, segmented image may be determined and plotted as a function of time that the image was acquired.

At 612, method 600 includes determining if a peak in the TUC signal has been detected, and if the detected peak is a plausible peak. For example, a peak detector may be executed that is configured to directly detect a peak in the TUC signal and evaluate whether the detected peak is the TUC peak (e.g., time point V on FIG. 3) by determining if the detected peak meets one or more rules that define the TUC peak. The peak detector may, for each CTP acquisition, look for a peak that has a double confirm (e.g., the peak may be double confirmed when two successive CTP acquisitions are performed, each having a lower measured HU than the detected peak). If a confirmed peak is found, the found peak is considered as an internal peak candidate (IPC). If the IPC occurs before a threshold time since the contrast injection (e.g., 14 seconds), the IPC may be discarded and the process may be repeated on the next IPC. If the IPC does not occur before the first threshold time, the IPC is further analyzed to determine if the slope of the IPC is greater than a threshold slope, such as 3 HU/s. If so, that IPC is considered a spike and is discarded. If not, the time between the ascent knee (e.g., time point U on FIG. 3) and the IPC is determined. If this time is less than a second threshold time, such as 4 seconds, the IPC is considered a spike and discarded. If not, it is determined if the median HU before the IPC is greater than a threshold value, such as the IPC HU minus 2. If so, the IPC is discarded. If not, the segmented tissue (e.g., brain) volume of the image acquisition at the IPC is compared to the segmented tissue volume from the previous image acquisition. If the segmented tissue volume at the IPC is different from the previous tissue volume by an amount that is greater than a threshold (e.g., 4.25%), the IPC is discarded. If not, (and if none of these described conditions are triggered), the IPC is confirmed as the tissue peak.

If a plausible TUC peak is detected in the TUC signal, method 600 proceeds to 614 to estimate an AIF curve, a VOF curve, and/or the remainder of the TUC from the TUC signal (and/or estimate the time for the arterial peak (AP), venous peak (VP), venous return to baseline (VRTB), and/or other time points of interest). The AIF and VOF curves and TUC may be estimated from the TUC signal by inputting the TUC signal into a machine learning model. As explained above, the TUC signal may include a measured segment of the TUC that may be used as input to a model, and the model may output the estimated AIF curve, the estimated VOF curve, and/or the remainder of the TUC. The model may be a suitable machine learning model, such as a decision tree, regression model, neural network, and so forth. The regression model may include a bootstrap algorithm that is trained with a dataset of N samples, where each sample includes a measured signal (whether entire AIF and VOF curves and/or TUC, or select features such as the inflection points on each curve, rate of change of various segments of the curves, curve peak times and heights, and/or curve knee times and heights) from a respective patient and identified (e.g., by an expert) ground truth, such as HU and time values for certain points of interest on the AIV, VOF, and TUC curves (e.g., A, B, C, Q, R, U, V, W), such that a plurality of measured signals and corresponding ground truths from a plurality of different patients are included in the dataset. The bootstrap algorithm creates random sub-samples of the dataset with replacement to output multiple values of a desired statistic, such as a mean. The average of those multiple values provides a robust estimate of the statistic. For example, the bootstrap algorithm may be applied to determine multiple values of each of a mean time to arterial peak, a mean time to venous peak, and a mean time to venous return to baseline, with each mean value correlated to an input measured signal. In some examples, the bootstrap algorithm may be aggregated where predictions (e.g., of the means described above) from multiple decision trees may be combined to reduce variance and overfitting. Cross-validation may be performed, where the input data (e.g., training dataset) is divided into n subsets, the regression model is trained with n−1 subsets, and the remaining subset is used to test the model to avoid overfitting.

In another example, the model may be a neural network that includes artificial neurons (referred to as units or nodes) arranged in a series of layers. The input units of the neural network receive information (e.g., the TUC signal), hidden units of the network process the information, the processed information is connected on positive or negative weights, and output units of the network signal a response to the learned information. In some examples, prior knowledge is used to reduce variance and improve generalizations and training data is run through the network and used to continuously change the weight vector of the network in response to a cost function, which improves the probability of an accurate output. In other words, the neural network may comprise a plurality of nodes/layers, including an input layer that receives the TUC signal and an output layer that outputs an estimated AIF curve, an estimated VOF curve, and/or estimated TUC (or estimated time to arterial peak, time to venous peak, time to venous return to baseline, and/or other time points), with connections/weights of the layers/nodes determined based on a training dataset. The training dataset may include a plurality of pairs of data, with each pair of data including measured contrast enhancement curves (e.g., AIF, VOF, TUC) and an associated TUC signal, or with each pair of data including a TUC signal and corresponding time points of interest for a plurality of patients (e.g., t_AP, t_VP, t_VRTB, etc.).

One or more zones of the CTP scan may then be identified base on the estimated AIF and VOF curves and/or the estimated time points of interest. As one example, a first zone may begin when the injection of contrast agent begins or the first zone may begin after a predefined delay after the injection has commenced. A first transition from the first zone to a second zone may be identified based on the venous peak (point Q). For example, the first transition may be estimated to occur two seconds after the venous peak. A second transition from the second zone to a third zone may be identified based on the venous return to baseline (VRTB, point R), for example, the second transition may be estimated to occur two seconds after the VRTB. The third zone may end at a fixed time after the VRTB, such as fourteen seconds after VRTB. Although three zones are described herein, the personalized CTP scan may include more or fewer than three zones without departing from the scope of this disclosure. For example, the first and second zones may be combined into a single zone, resulting in two zones, where the first zone has a relatively fast temporal sampling rate (e.g., one acquisition every 2 seconds). In another example, an additional zone may be appended after 14 seconds past VRTB (e.g., after the third zone), with the additional zone extending until 90 seconds post-VRTB and having a slower temporal sampling rate of one acquisition every 10 seconds.

In examples where the ML model outputs the estimated curves, the time points discussed herein (e.g., the VP and the VRTB) may be determined from the estimated curves. For example, the VRTB may be identified as the point on the VOF curve where the contrast level drops back below a threshold, or where the VOF curve slope switches from a negative rate of change to no change. The VP may be identified as the point of the VOF curve where the contrast level no longer increases (e.g., for a specified number of frames, such as two) and/or as the highest contrast level of the VOF curve.

At 616, one or more scan parameters are adjusted as the CTP scan progresses, based on the identified zones/zone transitions. For example, as explained above, values for one or more scan parameters may be adjusted for one or more zones, such as temporal sampling rate, tube current, tube voltage, etc. Adjusting the scan parameters may include decreasing the temporal sampling rate at each zone transition. For example, during the first zone, the temporal sampling rate may include one acquisition every 2 seconds. At the first transition, the temporal sampling rate may be decreased to one acquisition every 3-4 seconds (e.g., one acquisition every 3.5 seconds), and the temporal sampling rate may be at the decreased temporal sampling rate over the course of the second zone. At the second transition, the temporal sampling rate may again be decreased, for example to one acquisition every 5 seconds, until the end of the third zone. In some examples, the x-ray source current and voltage may remain constant across the entire CTP scan, regardless of the adjusted temporal sampling rates. In other examples, the x-ray source current and/or voltage may be adjusted. For example, the x-ray source current may be lowered for the second and/or third zones.

Thus, the adaptive CTP scan described herein may start at the first zone and may include scanning in the first zone at a first temporal sampling rate, first tube current, etc.; transitioning to the second zone at the first transition time (which may be based on the estimated VP as explained above) and scanning in the second zone at a second temporal sampling rate, second tube current, etc.; and transitioning to the third zone at the second transition time (which may be based on the estimated VRTB as explained above) and scanning in the third zone at a third temporal sampling rate, third tube current, etc. The scanning in the third zone may stop after a suitable number of acquisitions have been performed, such as three. In some examples, the first temporal sampling rate may be different than the second temporal sampling rate and the second temporal sampling rate may be different than the third temporal sampling rate. In some examples, one or more of the zones may have the same temporal sampling rate. In some examples, one or more of the zones may have the same tube current and/or one or more of the zones may have different tube current.

In some examples, method 600 may include updating the estimated TUC and AIF and VOF curves using an updated TUC signal obtained from coarse images reconstructed as the CTP scan progresses, as indicated at 618. For example, one or more images may be reconstructed from one or more of the CTP acquisitions, and the tissue segmentation and TUC signal measurement described above may be performed on these images to obtain an updated TUC signal that includes TUC data after the first portion of CTP acquisitions. This updated TUC signal may be entered into the machine learning model to provide an updated/refined estimate of the TUC and AIF and VOF curves.

At 620, one or more diagnostic images are reconstructed based on data acquired during the CTP scan. For example, one or more diagnostic images may be reconstructed using known reconstruction techniques, such as filtered back projection or iterative reconstruction. The images may be reconstructed based on data acquired from each CTP acquisition. Further, the image reconstruction of the diagnostic images may be performed in parallel with the coarse reconstruction described above, at least in some examples. The one or more diagnostic images may be output to a display device (e.g., display device 232) for display to an operator or a physician, to a storage medium (e.g., mass storage 218) for retrieving at a later time, and so on. Method 600 may then end.

Returning to 612, if a plausible peak is not detected, method 600 proceeds to 622 to determine if further monitoring for the TUC peak is justified. As explained above, monitoring for the TUC peak includes performing fast image reconstructions in order to segment the tissue of interest and measure the contrast level signal in the segmented tissue. These fast reconstructions, while less processing intensive than the actual diagnostic image reconstructions, still use up processing resources that could otherwise be devoted to performing the diagnostic image reconstructions. Thus, the fast image reconstructions performed as part of the TUC monitoring may delay the output of the final diagnostic images. Accordingly, any reduction in the overall scan time provided by the adaptive scan prescription may be weighed against the delay provided by the TUC monitoring. Further, the majority of patients may exhibit a TUC peak by 35 seconds after contrast agent injection, and thus if a TUC peak is not detected by a certain amount of time (e.g., 46-65 seconds), it may be likely that a plausible peak will not be detected.

Thus, an operator of the imaging system (or an administrator of the medical facility housing the imaging system, or another qualified personnel) may determine that continued monitoring for the TUC peak is not justified if the peak is not detected within a threshold amount of time, such as within 45-65 seconds. The determination of whether or not continued monitoring is justified may be made automatically based on the amount of elapsed time since the contrast agent was injected or the first CTP acquisition was performed relative to a threshold amount of time, which may be 45-65 seconds or another suitable time. The threshold time may be set in advance by the operator or another clinician or administrator. In some examples, the threshold time may selected by the operator (or other user) from a predefined range, such as 45-65 seconds. In another example, the determination of whether or not continued monitoring is justified may be made by the operator at the time of the CTP scan, such as via user input entered by the operator.

If it is determined at 622 that further monitoring is justified, method 600 proceeds to 624 to continue performing CTP acquisitions at the fallback parameters, such as at the fallback temporal sampling rate (e.g., of one acquisition every 2 seconds). Method 600 proceeds to 608 continue to reconstruct course images from the data acquired during the CTP acquisitions at the fallback parameters and continues to measure the TUC signal from the coarse images and monitor the TUC signal for a plausible peak. If further monitoring is not justified, for example if the TUC peak has not been detected after 45-65 seconds of monitoring, method 600 proceeds to 626 to continue CTP acquisitions at the fallback parameters until the CTP scan is complete. In such an example, the TUC signal monitoring is terminated, and all processing resources may be devoted to the diagnostic image reconstruction. Method 600 proceeds to 620 to reconstruct the diagnostic images, as explained above, and then method 600 ends.

Thus, the method described above with respect to FIG. 6 provides for a execution of a fallback CTP scan prescription that may be adapted on the fly based on individual patient contrast agent kinetics, in order to reduce the number of CTP acquisitions and/or reduce the duration of the CTP scan where possible. The adaptation of the fallback scan prescription may be performed only if a peak of a contrast signal is detected within a predetermined time frame, and may only be adapted to reduce the temporal sampling rate/move the transition times for reducing the temporal sampling rate (and ending the scan) to earlier time points. The fallback scan prescription may be a "worst case" CTP prescription with a longest scan duration and most number of passes/acquisitions. By initializing the CTP scan with the fallback prescription and then adapting if possible, rather than starting with a scan prescription that has a slower temporal sampling rate during the initial portion of the scan and then either adapting or switching to the fallback if the TUC peak cannot be identified, a more robust CTP scan may be performed for all patients.

In some examples, when the acquisitions are complete and as projection data is sent for image reconstruction/post-processing, the actual AIF/VOF curves (or TUC) may be generated as a first step to the perfusion map computation. In some examples, a post-scan workflow may include displaying to the user a comparison of the AIF/VOF/TUC estimates used to generate the CTP scan prescription vs the actual measured TUC and/or AIF and VOF curves. The differences between the estimated and measured AIF/VOF/TUC may be used to inform the user of the accuracy of the AIF/VOF estimates, inform the user of any errors in the estimates that might have impacted diagnostic image quality, and/or update the machine learning estimation models.

Further, while method 600 was described above with respect to a head CTP scan using a TUC signal to adapt the CTP scan prescription, the method may apply to other types of scans without departing from the scope of this disclosure. For example, the method may be used to adapt a liver CTP scan, a cardiac CTP scan, etc. Additionally, particularly when scanning other anatomical regions, an AIF signal may be monitored/used as the input to the ML model, rather than the TUC signal. In such examples, the AIF signal may be monitored for an AIF peak, in a manner similar to the peak detector described above. If a plausible AIF peak is detected, the AIF signal may be entered as input to the ML model to determine the VP and VRTB, for example, and then the CTP scan prescription may be adapted as described above. If no AIF peak is detected, the fallback scan prescription may be executed until the scan is complete.

FIG. 7 shows a set of plots 700 showing example CTP scan prescriptions for a first patient. A first plot 710 shows a fallback scan prescription. A second plot 720 shows how the fallback scan prescription is adapted based on the first patient's contrast signal. A third plot 730 shows the final adapted scan prescription along with measured AIF and VOF curves for the first patient.

Referring first to plot 710, it shows scanning events (with the tube current (mA) for each acquisition period of the CT imaging system) over time for the first patient according to the fallback scan prescription. A first acquisition may commence at time t1, after a prep delay (e.g., of 7 seconds) following contrast agent injection. The acquisitions of the CTP scan according to the fallback scan prescription may be carried out at the same first temporal sampling rate (e.g., of once every 2 seconds) until a first transition time, shown by time t2. At the first transition time, the temporal sampling rate may decrease, for example to one acquisition every 3.5 seconds. A second transition time is shown by time t3. At the second transition time, the temporal sampling rate may again decrease, for example to one acquisition every 5 seconds. The CTP scan may end at time t4. In the fallback scan prescription, the first transition time may be at 84 seconds, the second transition time may be at 87 seconds, and the scan may end at 92 seconds. As such, all but two acquisitions may be performed at the first, higher temporal sampling rate.

Next, plot 720 shows an adapted scan prescription for the first patient along with a first segment of a TUC curve 722 of the first patient, which may be the contrast signal (e.g., the TUC signal). The TUC curve may be measured as described above (e.g., from segmented tissue of the first patient). The adapted scan prescription commences at time t1 at the fallback temporal sampling rate, while the TUC signal is being monitored for the TUC peak. The TUC peak may be identified prior to time t2. Once the TUC peak is identified, the CTP scan prescription may be adapted based on the TUC signal. For example, the TUC signal may be entered into a ML model that may output the venous peak time and the venous return to baseline time. The CTP scan prescription may be adapted to move the first transition time (shown by time t2), the second transition time (shown by time t3), and the end of the scan (shown by time t4) to the left (e.g., earlier in time) relative to the fallback scan prescription. For example, as shown in plot 720, the first transition time may be at about 34 seconds, the second transition time may be at about 45 seconds, and the scan may end at about 60 seconds. In this way, multiple acquisitions may be performed at a second, lower temporal sampling rate (e.g., four acquisitions performed between t2 and t3) and multiple acquisitions may be performed at a third, even lower temporal sampling rate (e.g., four acquisitions performed between t3 and t4).

The adjustment of the transition times for the adapted scan prescription may be based on the output of the ML model, using the TUC signal as input. For example, the ML model may output a predicted time to the venous peak (VP) of the VOF curve and a predicted time to the venous return to baseline (VRTB) of the VOF curve, and the transition times may be moved according to the predicted VP and predicted VRTB. For example, the first transition time may be moved to be at or after the VP (e.g., 2 seconds after the VP) and the second transition time may be moved to be at or after the VRTB (e.g., 2 seconds after the VRTB). The end of the scan may be moved to be at a fixed time after the VRTB, such as 14 seconds after the VRTB.

Plot 730 shows the adapted scan prescription of plot 720 overlaid on a measured AIF curve 732 and a measured VOF curve 734 for the first patient. The VOF curve may be measured as explained above (e.g., at a vein of the patient). As appreciated by plot 730, the first transition time at time t2 is at the VP of the VOF curve 734 and the second transition time at time t3 is at the VRTB of the VOF curve 734.

FIG. 8 shows a set of plots 800 showing example CTP scan prescriptions for a second patient. The first plot 710 shows a fallback scan prescription. A second plot 820 shows how the fallback scan prescription is adapted based on the second patient's contrast signal. A third plot 830 shows the final adapted scan prescription along with measured AIF and VOF curves for the second patient. Plot 710 of FIG. 8 is the same as plot 710 of FIG. 7, and thus includes the temporal sampling rates and transition times discussed above.

Plot 820 shows an adapted scan prescription for the second patient along with a first segment of a TUC curve 822 of the second patient. The adapted scan prescription commences at time t1 at the fallback temporal sampling rate, while the TUC signal is being monitored for the TUC peak. The TUC peak may be identified prior to time t2, for example at time t1'. Once the TUC peak is identified, the CTP scan prescription may be adapted based on the TUC signal. The CTP scan prescription may be adapted to move the first transition time (shown by time t2), the second transition time (shown by time t3), and the end of the scan (shown by time t4) to the left (e.g., earlier in time) relative to the fallback scan prescription. For example, as shown in plot 820, the first transition time may be at about 28 seconds, the second transition time may be at about 38 seconds, and the scan may end at about 50 seconds. In this way, multiple acquisitions may be performed at a second, lower temporal sampling rate (e.g., three acquisitions performed between t2 and t3) and multiple acquisitions may be performed at a third, even lower temporal sampling rate (e.g., four acquisitions performed between t3 and t4).

The adjustment of the transition times for the adapted scan prescription may be based on the output of the ML model, using the TUC signal as input. For example, the ML model may output a predicted time to the venous peak (VP) of the VOF curve and a predicted time to the venous return to baseline (VRTB) of the VOF curve, and the transition times may be moved according to the predicted VP and predicted VRTB. For example, the first transition time may be moved to be at or after the VP (e.g., 2 seconds after the VP) and the second transition time may be moved to be at or after the VRTB (e.g., 2 seconds after the VRTB). The end of the scan may be moved to be at a fixed time after the VRTB, such as 14 seconds after the VRTB.

Plot 830 shows the adapted scan prescription of plot 820 overlaid on a measured AIF curve 832 and a measured VOF curve 834 for the second patient. As appreciated by plot 830, the first transition time at time t2 is just after the VP of the VOF curve 834 and the second transition time at time t3 is just after the VRTB of the VOF curve 834.

FIG. 9 shows a set of plots 900 showing example CTP scan prescriptions for a third patient. The first plot 710 shows a fallback scan prescription. A second plot 920 shows how the fallback scan prescription is adapted based on the third patient's contrast signal. A third plot 930 shows the final adapted scan prescription along with measured AIF and VOF curves for the third patient. Plot 710 of FIG. 9 is the same as plot 710 of FIG. 7, and thus includes the temporal sampling rates and transition times discussed above.

Plot 920 shows an adapted scan prescription for the third patient along with a first segment of a TUC curve 922 of the third patient. The adapted scan prescription commences at time t1 at the fallback temporal sampling rate, while the TUC signal is being monitored for the TUC peak. The TUC peak may be identified prior to time t2, for example at time t1'. Once the TUC peak is identified, the CTP scan prescription may be adapted based on the TUC signal. The CTP scan prescription may be adapted to move the first transition time (shown by time t2), the second transition time (shown by time t3), and the end of the scan (shown by time t4) to the left (e.g., earlier in time) relative to the fallback scan prescription. For example, as shown in plot 920, the first transition time may be at about 38 seconds, the second transition time may be at about 58 seconds, and the scan may end at about 70 seconds. In this way, multiple acquisitions may be performed at a second, lower temporal sampling rate (e.g., seven acquisitions performed between t2 and t3) and multiple acquisitions may be performed at a third, even lower temporal sampling rate (e.g., four acquisitions performed between t3 and t4).

The adjustment of the transition times for the adapted scan prescription may be based on the output of the ML model, using the TUC signal as input. For example, the ML model may output a predicted time to the venous peak (VP) of the VOF curve and a predicted time to the venous return to baseline (VRTB) of the VOF curve, and the transition times may be moved according to the predicted VP and predicted VRTB. For example, the first transition time may be moved to be at or after the VP (e.g., 2 seconds after the VP) and the second transition time may be moved to be at or after the VRTB (e.g., 2 seconds after the VRTB). The end of the scan may be moved to be at a fixed time after the VRTB, such as 14 seconds after the VRTB.

Plot 930 shows the adapted scan prescription of plot 920 overlaid on a measured AIF curve 932 and a measured VOF curve 934 for the first patient. As appreciated by plot 930, the first transition time at time t2 is just after the VP of the VOF curve 934 and the second transition time at time t3 is just after the VRTB of the VOF curve 934.

FIG. 9 also demonstrates that the peak detector that is deployed to identify a plausible TUC peak may discard peaks that do not fit the criteria for the TUC peak. For example, plot 920 shows two peaks before the TUC peak, a peak at 6 seconds and a peak at 8 seconds. Because both of these peaks occur before a threshold time (e.g., 14 seconds), the peaks are discarded as being candidates for the TUC peak, and the TUC signal continues to be generated and monitored until the TUC peak is identified (e.g., at time t1').

As appreciated from FIGS. 7-9, the first, second, and third patients have different contrast agent kinetics, resulting in different adapted CTP scan prescriptions. For example, the first patient may have a TUC peak that is identified later than the TUC peak of the second patient, and thus the first patient may be scanned for a longer duration than the second patient. The third patient may be scanned for an even longer duration than the first patient. However, because a TUC peak is identified for each of the first, second, and third patients, the patients are all scanned for a shorter duration than the duration of the fallback scan prescription, and fewer acquisitions are performed in each of the adapted scan prescriptions than the fallback scan prescription.

FIG. 10 shows a set of plots 1000 showing example CTP scan prescriptions for a fourth patient. The first plot 710 shows a fallback scan prescription. A second plot 1020 shows how the fallback scan prescription is adapted based on the fourth patient's contrast signal. Plot 710 of FIG. 10 is the same as plot 710 of FIG. 7, and thus includes the temporal sampling rates and transition times discussed above.

Plot 1020 shows the scan prescription for the fourth patient along with a first segment of a TUC curve 1022 of the fourth patient. The scan prescription commences at time t1 at the fallback temporal sampling rate, while the TUC signal is being monitored for the TUC peak. However, as appreciated in plot 1020, a TUC peak is not identified before a threshold amount of time, shown by time t1', which as shown is at 60 seconds. As explained above, the two peaks that occur early in the TUC monitoring are discarded as candidate TUC peaks, and no other peaks occur before the threshold time. Thus, the fallback scan prescription may be maintained for the entirety of the CTP scan for the fourth patient, and the TUC monitoring may end at the threshold time.

Thus, as disclosed herein, a CTP scan may commence according to a fallback scan prescription, where a plurality of acquisitions are performed at a first, higher temporal sampling rate. The projection data that is acquired in the plurality of acquisitions is processed to measure a contrast signal of the contrast agent, which is monitored to determine if a peak in the contrast signal is detected. If the peak in the contrast signal is detected within a predetermined time frame, the fallback scan prescription is updated to generate an adapted scan prescription for the contrast scan based on the contrast signal, and a remainder of the contrast scan is performed according to the adapted scan prescription. However, if a peak in the contrast signal is not detected within the predetermined time frame, the remainder of the contrast scan is continued according to the fallback scan prescription that was originally initialized. The fallback scan prescription is independent of the contrast signal. For example, the fallback scan prescription includes a plurality of acquisitions being performed at a first temporal sampling rate for a first duration (e.g., the acquisitions performed between time t1 and time t2 of plot 710 of FIGS. 7-10), one or more acquisitions being performed at a second temporal sampling rate for a second duration (e.g., the acquisition performed between time t2 and time t3 of plot 710), and one or more acquisitions being performed at a third temporal sampling rate for a third duration (e.g., the acquisitions performed between time t3 and time t4 of plot 710), with the scan ending at time t4. The first, second, and third durations may each be fixed, such that the durations are the same regardless of the patient.

In contrast, the adapted scan prescription is dependent on the contrast signal. For example, the adapted scan prescription includes a plurality of acquisitions being performed at the first temporal sampling rate for a first duration (e.g., the acquisitions performed between time t1 and time t2 of plots 720, 820, and 920 of FIGS. 7-9), one or more acquisitions being performed at a second temporal sampling rate for a second duration (e.g., the acquisition performed between time t2 and time t3 of plots 720, 820, and 920), and one or more acquisitions being performed at a third temporal sampling rate for a third duration (e.g., the acquisitions performed between time t3 and time t4 of plots 720, 820, and 920), with the scan ending at time t4. The first, second, and third durations may each be dependent on the contrast signal, such that the durations may be different for different patients. In particular, the first duration of the adapted scan prescription may be dependent on the patient's venous peak, which may be estimated based on the contrast signal, the second duration of the adapted scan prescription may be dependent on the patient's venous peak and venous return to baseline, as determined from the contrast signal, and the third duration of the adapted scan prescription may be dependent on the patient's venous return to baseline, as determined from the contrast signal.

As such, the fallback scan prescription may include a first time point where the first temporal sampling rate transitions to the second temporal sampling rate (time t2 in plot 710), and this first time point is fixed relative to the beginning of the contrast scan and is independent of the patient and the contrast signal. The adapted scan prescription may include a second time point where the first temporal sampling rate transitions to the second temporal sampling rate (time t2 in plots 720, 820, and 920), and this second time point may change based on the contrast signal. For example, if the peak of the contrast signal is detected, the second time point may be shifted relative to the first time point based on the contrast signal, such that the second time point is earlier than the first time point, thereby shortening the first duration of the adapted scan prescription relative to the first duration of the fallback scan prescription. The adapted scan prescription may also end earlier than the fallback scan prescription. While a third time point of the adapted scan prescription (e.g., where the second temporal sampling rate transitions to the third temporal sampling rate, time t3 of plots 720, 820, and 920) may be shifted to be earlier than a corresponding fourth time point of the fallback scan prescription, each of the second duration and the third duration of the adapted scan prescription may be longer than the respective second duration and third duration of the fallback scan prescription, at least in some examples. In doing so, a higher proportion of the adapted scan prescription may be carried out the second and/or third temporal sampling rate relative to the fallback scan prescription, which may be lower than the first temporal sampling rate and thus may subject the patient to less radiation.

Thus, the systems and methods disclosed herein provide for estimating when various contrast agent time points/curves will occur for a specific patient, using (at least initially) a short measured segment (referred to as a contrast signal) of a contrast enhancement curve measured at a monitoring area as an input to a machine learning model to predict the remaining contrast agent time points or curves. The contrast enhancement curve may be an arterial inflow function (AIF) curve, and the segment of the AIF curve may be measured at an artery of the patient, in an example. In another example, the contrast enhancement curve may be a venous outflow function (VOF) curve, and the segment of the VOF curve may be measured at a vein of the patient. In a still further example, the contrast enhancement curve may be a tissue uptake curve (TUC), and the segment may be measured at a tissue of interest (e.g., the brain), where the tissue is segmented in a plurality of images. In some examples, more than one contrast enhancement curve may be measured (e.g., both the AIF and the VOF may be measured). Based on these estimated time points, various contrast scan actions may be carried out. As explained above with respect to FIG. 6, the predicted time points may be used to adapt a CTP scan prescription. The adapted CTP scan prescription may be carried out with a single contrast injection, and the time points may be estimated using a measured segment of a contrast enhancement curve of the single contrast injection.

The time points may be estimated from an AIF signal or a TUC signal. As explained above with respect to FIGS. 3-5, the AIF signal may be a segment of an AIF curve measured at an arterial ROI and the TUC signal may be a segment of a TUC measured at a segmented tissue region. The TUC signal may be robust to patient movement, given that the "ROI" is the segmented tissue and thus the ROI moves along with the patient from image to image. Further, the TUC signal may be measured at the head, rather than the neck, which may eliminate the need to adjust the imaging region of interest to go between the measurement of the TUC signal and diagnostic acquisitions.

Each estimation method includes a model. In the training for the models, if the AIF segment is the input, the measured signal for training the model is the AIF curve segment and/or features from the AIF curve segment. The ground truth for training the model may be the collection of times for A, B, C, P, Q, and R on the AIF and VOF curves and possibly HU values as well. If the TUC segment is the input, the measured signal for training the model is the TUC curve segment and/or features from the TUC curve segment. The ground truth for training may be same as above (e.g., A, B, C, P, Q, and R times and possibly HU values as well).

In any of the methods described herein, once the time points have been estimated and the scan protocols adjusted (or not) based on the estimated time points, the AIF or TUC signal may continue to be measured in order to determine an actual AIF curve, VOF curve, and/or TUC. If an acquisition timed based on an estimated time point is determined to have been acquired at an incorrect time, an operator may be notified so that the acquisition may be repeated at the correct time. This may include performing an additional scan, with an additional contrast agent bolus, but may reduce undue reconstruction time, as the operator may be notified before full diagnostic reconstruction has begun, rather than waiting until the diagnostic images have been reconstructed to determine that one or more scans did not produce sufficient diagnostic images. Further, in any of the methods described herein, when the acquisitions are complete and as projection data is sent for image reconstruction/post-processing, the actual AIF/VOF/TUC curves may be generated and displayed to the user as comparison of the AIF/VOF/TUC estimates used to generate the scan prescription(s) described herein versus the actual measured AIF, VOF, and/or TUC curves. The differences between the estimated and measured AIF/VOF/TUC curves may be used to inform the user of the accuracy of the AIF/VOF/TUC estimates, inform the user of any errors in the estimates that might have impacted diagnostic image quality, and/or update the machine learning estimation models.

A technical effect of the disclosure is that an adaptive, personalized multiple zone perfusion scan may be performed, which may increase diagnostic image quality and/or reduce patient radiation exposure, without compromising scan quality for patients whose contrast agent kinetics cannot be reasonable estimated within the time frame of the scan protocol. A further technical effect of the disclosure is that scan durations may be reduced and subsequent patient treatment decisions may be more accurate, reducing unnecessary transfers to other medical facilities and improving patient outcomes.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
   upon an injection of a contrast agent, initiating a contrast scan of a subject according to a fallback scan prescription, the fallback scan prescription including fixed durations for acquiring projection data at different temporal sampling rates relative to a beginning of the contrast scan;
   processing acquired projection data of an anatomical region of interest (ROI) of the subject to measure a contrast signal of the contrast agent;
   identifying a peak in the contrast signal within a predetermined time frame;
   if the peak is identified within the predetermined time frame, updating the fallback scan prescription to generate an adapted scan prescription for the contrast scan based on the contrast signal, including adjusting at least one of the fixed durations based on the contrast signal, and performing a remainder of the contrast scan according to the adapted scan prescription; and if the peak in the contrast signal is not identified within the predetermined time frame, continuing the remainder of the contrast scan according to the fallback scan prescription.

2. The method of claim 1, wherein the fixed durations for acquiring projection data at different temporal sampling rates of the fallback scan prescription include a first duration for acquiring projection data at a first temporal sampling rate, a second duration for acquiring projection data at a second temporal sampling rate, and a third duration for acquiring projection data at a third temporal sampling rate.

3. The method of claim 2, wherein updating the fallback scan prescription to generate the adapted scan prescription for the contrast scan based on the contrast signal comprises adjusting at least one of the first duration, the second duration, and the third duration based on the contrast signal.

4. The method of claim 3, wherein adjusting at least one of the first duration, the second duration, and the third duration based on the contrast signal comprises decreasing at least the first duration such that the adapted scan prescription transitions to the second temporal sampling rate earlier than the fallback scan prescription.

5. The method of claim 3, wherein adjusting at least one of the first duration, the second duration, and the third duration based on the contrast signal comprises entering the contrast signal as input to a machine learning model configured to output a plurality of time points of an arterial inflow function curve, a tissue uptake curve, and/or a venous outflow function curve based on the contrast signal, and wherein the first duration and/or the second duration, and/or the third duration are adjusted as a function of a respective one of the plurality of time points.

6. The method of claim 2, wherein the first temporal sampling rate is higher than the second temporal sampling rate and the second temporal sampling rate is higher than the third temporal sampling rate.

7. The method of claim 2, wherein initiating the contrast scan of the subject according to the fallback scan prescription and continuing the remainder of the contrast scan according to the fallback scan prescription comprise performing a plurality of acquisitions at the first temporal sampling rate for the first duration, performing one or more acquisitions at the second temporal sampling rate for the second duration, performing one or more acquisitions at the third temporal sampling rate for the third duration, and terminating the contrast scan at an end of the third duration.

8. The method of claim 1, wherein the acquired projection data of the anatomical ROI used to measure the contrast signal is acquired while the fallback scan prescription is being performed.

9. The method of claim 1, wherein processing projection data of the anatomical ROI to measure the contrast signal comprises reconstructing a plurality of images from the projection data, segmenting a tissue of interest in each image of the plurality of images, measuring a signal intensity of the segmented tissue in each image relative to a baseline, and plotting each signal intensity as a function of time to generate the contrast signal.

10. A method for an imaging system, comprising:
upon an injection of a contrast agent, performing a contrast scan of an anatomical region of interest (ROI) of a subject at a first temporal sampling rate;
processing projection data of the anatomical ROI acquired during the contrast scan to measure a contrast signal of the contrast agent;
identifying a peak in the contrast signal within a predetermined time frame;

if the peak in the contrast signal is identified within the predetermined time frame, adjusting the first temporal sampling rate to a second temporal sampling rate at a first transition time that is determined based on the contrast signal; and
if the peak in the contrast signal is not identified within the predetermined time frame, adjusting the first temporal sampling rate to the second temporal sampling rate at a second transition time that is a fixed duration relative to a beginning of the contrast scan and independent of the contrast signal.

11. The method of claim 10, wherein the first temporal sampling rate is faster than the second temporal sampling rate.

12. The method of claim 10, wherein adjusting the first temporal sampling rate to the second temporal sampling rate at the first transition time that is determined based on the contrast signal comprises entering the contrast signal as input to a machine learning model, the machine learning model configured to output a plurality of estimated time points, including an estimated arterial peak time, an estimated venous peak time, and an estimated venous return to baseline time, and determining when the first transition time is estimated to occur based on one of the plurality of estimated time points.

13. The method of claim 12, wherein determining when the first transition time is estimated to occur based one of the plurality of estimated time points comprises determining when the first transition time is estimated to occur as a function of the estimated venous peak time.

14. The method of claim 13, further comprising identifying the peak in the contrast signal within the predetermined time frame, and if the peak is identified within the predetermined time frame, determining when a third transition time is estimated to occur as a function of the estimated venous return to baseline time, and adjusting the second temporal sampling rate to a third temporal sampling rate at the third transition time.

15. The method of claim 14, further comprising if the peak in the contrast signal is not identified within the predetermined time frame, adjusting the second temporal sampling rate to the third temporal sampling rate at a fourth transition time that is independent of the contrast signal.

16. A system, comprising:
an x-ray source that emits a beam of x-rays toward a subject to be imaged;
a detector that receives the x-rays attenuated by the subject;
a data acquisition system (DAS) operably connected to the detector; and
a computer operably connected to the DAS and configured with instructions in non-transitory memory that when executed cause the computer to:
upon an injection of a contrast agent, initiate a contrast scan of an anatomical region of interest (ROI) of the subject according to a fallback scan prescription;
process projection data from the DAS during a portion of the contrast scan to measure a contrast signal of the contrast agent;
identify a peak in the contrast signal prior to a threshold time;
if the peak in the contrast signal is identified within the threshold time, perform a remainder of the contrast scan according to an adapted scan prescription that is dependent on the contrast signal, the adapted scan prescription including a transition to a lower temporal sampling rate at a first time point that is based on the contrast signal; and if the peak in the contrast signal is not identified prior to the threshold time, complete the remainder of the contrast scan according to the fallback scan prescription, where the fallback scan prescription is independent of the contrast signal, the fallback scan prescription including the transition to the lower temporal sampling rate at a second time point that is a fixed duration relative to a beginning of the contrast scan and independent of the contrast signal.

17. The system of claim 16, wherein the non-transitory memory stores a machine learning model configured to determine when the first time point is estimated to occur based on the contrast signal.

18. The system of claim 17, wherein the machine learning model is a regression model or a neural network.

19. The system of claim 16, wherein the threshold time is selected from a predefined time range via user input.

* * * * *